US006413530B1

(12) United States Patent
Borovsky et al.

(10) Patent No.: US 6,413,530 B1
(45) Date of Patent: Jul. 2, 2002

(54) PESTICIDAL PEPTIDES

(75) Inventors: Dov Borovsky, Vero Beach, FL (US); Russell J. Linderman, Raleigh, NC (US)

(73) Assignees: University of Florida Research Foundation, Inc., Gainesville, FL (US); North Carolina State University, Raleigh, NC (US)

( * ) Notice: Subject to any disclaimer, the term of this patent is extended or adjusted under 35 U.S.C. 154(b) by 0 days.

(21) Appl. No.: 09/295,996

(22) Filed: Apr. 21, 1999

(51) Int. Cl.[7] .......................... A01N 25/00; A61K 38/00; C07K 7/00; C07K 16/00; C07K 17/00

(52) U.S. Cl. .......................... 424/405; 514/2; 514/875; 514/919; 530/300; 530/329; 530/330; 530/331

(58) Field of Search ................................ 530/300, 329, 530/330, 331; 514/2, 875, 919; 424/405

(56) References Cited

U.S. PATENT DOCUMENTS

| | | | | |
|---|---|---|---|---|
| 5,011,909 | A | 4/1991 | Borovsky et al. | 530/328 |
| 5,130,253 | A | 7/1992 | Borovsky et al. | 535/320.1 |
| 5,358,934 | A | 10/1994 | Borovsky et al. | 514/17 |
| 5,439,821 | A | 8/1995 | Borovsky et al. | 435/240.2 |
| 5,501,976 | A | 3/1996 | Borovsky et al. | 435/252.3 |
| 5,849,525 | A | * 12/1998 | Hediger | 435/69.1 |

FOREIGN PATENT DOCUMENTS

| | | |
|---|---|---|
| EP | 0412595 | 2/1991 |
| JP | 01226898 | 9/1989 |
| JP | 07188282 | 7/1995 |

OTHER PUBLICATIONS

Narberhaus et al., J. Bacteriol. vol. 178, pp. 5337–5346, 1996.*

Gauthier et al., Plant. Physiol. vol. 108, p. 1341, 1995.*

Hlavacek et al., Bioorg. Chem., vol. 26, pp. 131–140, Oct., 1998.*

Borovsky, Dov (1985) "Isolation and Characterization of Highly Purified Mosquito Oostatic Hormone" *Archives of Insect Biochemistry and Physiology* 2:333–349.

Borovsky, Dov (1988) "Oostatic Hormone Inhibits Biosynthesis of Midgut Proteolytic Enzymes and Egg Development in Mosquitoes" *Archives of Insect Biochemistry and Physiology* 7:187–210.

Borovsky, Dov (1990) "Mosquito oostatic factor: a novel decapeptide modulating trypsin–like enzyme biosynthesis in the midgut" *The FASEB Journal* 4:3015–3019.

Borovsky, Dov, C.A. Powell, J.K. Nayar, J. Edwin Blalock, T.K. Hayes (1994) "Characterization and localization of mosquito–gut receptors for trypsin modulating oostatic factor using a complementary peptide and immunocytochemistry" *The FASEB Journal* 8:350–355.

Borovsky, Dov, Farida Mahmood (1995) "Feeding the mosquito *Aedes aegypti* with TMOF and its analogs; effect on trypsin biosynthesis and egg development" *Regulatory Peptides* 57:273–281.

Curry, W.J., C. Shaw, C.F. Johnston, L. Thim, K.D. Buchanan (1992) "Neuropeptide F: Primary Structure From The Tubellarian, *Artioposthia triangulata*" *Comp. Biochem. Physiol.* 101C(2):269–274.

Duve, Hanne, Alan Thorpe, Ray Neville, Norman R. Lazarus (1981) "Isolation and partial characterization of pancreatic polypeptide–like material in the brain of the blowfly *Calliphora vomitoria*" *J. Biochem.* 197:767–770.

Leung, P.S., C. Shaw, A.G. Maule, L. Thim, C.F. Johnston, G.B. Irvine (1992) "The primary structure of neuropeptide F (NPF) from the garden snail, *Helix aspersa*" *Regulatory Peptides* 41:71–81.

Maule et al. (1991) "Neuropeptide F: a novel parasitic flatworm regulatory peptide from *Moniezia expansa* (Cestoda: Cyclophyllidea)" *Parasitology* 102:309–316.

Rajpara, Sanjay M., et al. (1992) "Identification and Molecular Cloning of a Neuropeptide Y Homolog That Produces Prolonged Inhibition in Aplysia Neurons" *Neuron* 9:505–513.

Spittaels, Kurt, Peter Verhaert, Christ Shaw, Richard N. Johnston, Bart Devreese, Jos Van Beeumen, Arnold De Loof (1996) "Insect Neuropeptide F (NPF)–related Peptides: Isolation from Colorado Potato Beetle (*Leptinotarsa decemlineata*) Brain" *Insect Biochem. Molec. Biol.* 26(4):375–382.

Veenstra, J.A., H.M. Romberg–Privee, H. Schooneveld, J.M. Polak (1985) "Immunocytochemical localization of peptidergic neurons and neurosecretory cells in the neuro–endocrine system of the Colorado potato beetle with antisera to vertebrate regulatory peptides" *Histochemistry* 82:9–18.

Verhaert, Peter, Cornelis J. P. Grimmelikhuijzen, Arnold De Loof (1985) "Distinct Localization of FMRFamide– and Bovine Pancreatic Polypeptide–Like Material in the Brain, Retrocerebral Complex and Suboesophageal Ganglion of the Cockroach *Periplaneta americana* L." *Brain Research* 348:331–338.

Shibnev, V. A. et al. (Jun. 23, 1969) "Synthesis of monomers that are triplets of the "crystalline " part of the collagen molecule" *Chemical Abstracts*, vol. 70, No. 25, abstract No. 115551, Columbus, Ohio.

Henderson, David E. et al. (May 21, 1990) "Physicochemical studies of biologically active peptides by low–temperature reversed–phase high–performance liquid chromatography" *Chemical Abstracts* vol. 112, No. 21, abstract No. 192024, Columbus, Ohio.

(List continued on next page.)

*Primary Examiner*—Yvonne Eyler
*Assistant Examiner*—Janet L. Andres
(74) *Attorney, Agent, or Firm*—Saliwanchik, Lloyd & Saliwanchik

(57) ABSTRACT

The subject invention pertains to novel pest control compounds. Specifically exemplified herein are peptides having 2 to 5 amino acids. The subject peptides are useful against a variety of pests, including pests of agricultural crops.

37 Claims, No Drawings

OTHER PUBLICATIONS

Okada et al. (Nov. 7, 1977) "Synthesis of bradykinin fragments and their effect on pentobarbital sleeping time in mouse" *Chemical Abstracts* vol. 87, No. 19, abstract No. 146142, Columbus, Ohio.

Ladram et al. (1992) "Characterization of receptors for thyrotropin–releasing hormone–receptors potentiating peptide on rat anterior pituitary membranes" *J. Biol. Chem.* 267(36):25697–25702.

Bordusa et al. (1998) "The specificity of prolyl endopeptidase from *Flavobacterium meningoseptum*: mapping the S' subsites by positional scanning via acyl transfer" *Bioorg. Med. Chem.* 6(10):1775–1780.

Deslauriers et al. (1979) "Steric effects of cis–trans isomerism on neighboring residues in proline oligopeptides: as carbon–13 NMR study of conformational heterogeneity in linear tripeptides" *Biopolymers* 18(3):523–538.

Kolaskar et al. (1983) "Conformational properties of pairs of amino acids" *Int. J. Pept. Protein Res.* 22(1):83–91.

Tykva, Richard et al. (Jun. 26, 2000) *Chemical Abstracts*, vol. 132(26), abstract No. 345576.

* cited by examiner

SEQUENCE LISTING

```
<160> NUMBER OF SEQ ID NOS: 60

<210> SEQ ID NO 1
<211> LENGTH: 10
<212> TYPE: PRT
<213> ORGANISM: Leptinotarsa decemlineata
<220> FEATURE:
<221> NAME/KEY: MOD_RES
<222> LOCATION: (10)..(10)
<223> OTHER INFORMATION: AMIDATION

<400> SEQUENCE: 1

Ala Arg Gly Pro Gln Leu Arg Leu Arg Phe
1               5                   10


<210> SEQ ID NO 2
<211> LENGTH: 8
<212> TYPE: PRT
<213> ORGANISM: Leptinotarsa decemlineata
<220> FEATURE:
<221> NAME/KEY: MOD_RES
<222> LOCATION: (8)..(8)
<223> OTHER INFORMATION: AMIDATION

<400> SEQUENCE: 2

Ala Pro Ser Leu Arg Leu Arg Phe
1               5


<210> SEQ ID NO 3
<211> LENGTH: 378
```

-continued

```
<212> TYPE: DNA
<213> ORGANISM: Aedes aegypti
<220> FEATURE:
<221> NAME/KEY: CDS
<222> LOCATION: (1)..(189)
<223> OTHER INFORMATION:

<400> SEQUENCE: 3

ata ctg ggg agg ggg ggg ggg gac att ggg tta ctc agt tca gac caa       48
Ile Leu Gly Arg Gly Gly Gly Asp Ile Gly Leu Leu Ser Ser Asp Gln
1               5                   10                  15

agg agt ttc agc act gaa act ctg ctt aaa gaa cta aaa aga gaa gcg       96
Arg Ser Phe Ser Thr Glu Thr Leu Leu Lys Glu Leu Lys Arg Glu Ala
            20                  25                  30

gcg gct gag gag cgg agt gct gcc tcc aac tcg ggg tcg gtg gtt ccc      144
Ala Ala Glu Glu Arg Ser Ala Ala Ser Asn Ser Gly Ser Val Val Pro
        35                  40                  45

ctc tcg gag caa agg ctg atg gga cat ctg gcg gcc gcg ctg tga          189
Leu Ser Glu Gln Arg Leu Met Gly His Leu Ala Ala Ala Leu
    50                  55                  60

gccggctttc ctgctgccac tttgggcgcc ttggatggag atcccaattg cagtttgtat    249

tttatttttt tataagggac acgtggaaaa accaaaccaa accaaacaaa gccaacaaac    309

cacgacggtc cttattttaa acctcagact ccataaagaa acctttctat ccaaaaaaaa    369

aaaaaaaaa                                                            378


<210> SEQ ID NO 4
<211> LENGTH: 62
<212> TYPE: PRT
<213> ORGANISM: Aedes aegypti

<400> SEQUENCE: 4

Ile Leu Gly Arg Gly Gly Gly Asp Ile Gly Leu Leu Ser Ser Asp Gln
1               5                   10                  15

Arg Ser Phe Ser Thr Glu Thr Leu Leu Lys Glu Leu Lys Arg Glu Ala
            20                  25                  30

Ala Ala Glu Glu Arg Ser Ala Ala Ser Asn Ser Gly Ser Val Val Pro
        35                  40                  45

Leu Ser Glu Gln Arg Leu Met Gly His Leu Ala Ala Ala Leu
    50                  55                  60


<210> SEQ ID NO 5
<211> LENGTH: 10
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Can be Ala, Asp, Phe, Gly, Met, Pro, Ser, or
      Tyr
<220> FEATURE:
<221> NAME/KEY: MISC_FEATURE
<222> LOCATION: (2)..(2)
<223> OTHER INFORMATION: Can be Ala, Asp, Glu, Phe, Gly, Asn, Pro,
      Ser, or Tyr.
<220> FEATURE:
<221> NAME/KEY: MISC_FEATURE
<222> LOCATION: (3)..(3)
<223> OTHER INFORMATION: Is optionally present and can be Ala, Asp,
      Phe, Gly, Leu, Pro, Ser, or Tyr.
<220> FEATURE:
<221> NAME/KEY: MISC_FEATURE
<222> LOCATION: (4)..(4)
<223> OTHER INFORMATION: Is optionally present and can be Ala, Phe,
```

-continued

```
      Gly, Leu, or Tyr.
<220> FEATURE:
<221> NAME/KEY: MISC_FEATURE
<222> LOCATION: (5)..(5)
<223> OTHER INFORMATION: Is optionally present and can be Ala, Phe,
      Leu, or Pro.
<220> FEATURE:
<221> NAME/KEY: MISC_FEATURE
<222> LOCATION: (6)..(10)
<223> OTHER INFORMATION: Each of amino acids 6-10 are optionally
      present.

<400> SEQUENCE: 5

Xaa Xaa Xaa Xaa Xaa Pro Pro Pro Pro Pro
1               5                   10


<210> SEQ ID NO 6
<211> LENGTH: 4
<212> TYPE: PRT
<213> ORGANISM: Artificial Sequence
<220> FEATURE:
<223> OTHER INFORMATION: Flanking region

<400> SEQUENCE: 6

Pro Pro Pro Pro
1


<210> SEQ ID NO 7
<211> LENGTH: 5
<212> TYPE: PRT
<213> ORGANISM: Artificial Sequence
<220> FEATURE:
<223> OTHER INFORMATION: Flanking region

<400> SEQUENCE: 7

Pro Pro Pro Pro Pro
1               5


<210> SEQ ID NO 8
<211> LENGTH: 10
<212> TYPE: PRT
<213> ORGANISM: Aedes aegypti

<400> SEQUENCE: 8

Tyr Asp Pro Ala Pro Pro Pro Pro Pro Pro
1               5                   10


<210> SEQ ID NO 9
<211> LENGTH: 10
<212> TYPE: PRT
<213> ORGANISM: Artificial Sequence
<220> FEATURE:
<223> OTHER INFORMATION: TMOF peptide

<400> SEQUENCE: 9

Asp Tyr Pro Ala Pro Pro Pro Pro Pro Pro
1               5                   10


<210> SEQ ID NO 10
<211> LENGTH: 8
<212> TYPE: PRT
<213> ORGANISM: Artificial Sequence
<220> FEATURE:
<223> OTHER INFORMATION: TMOF peptide

<400> SEQUENCE: 10

Pro Ala Pro Pro Pro Pro Pro Pro
1               5
```

-continued

<210> SEQ ID NO 11
<211> LENGTH: 5
<212> TYPE: PRT
<213> ORGANISM: Artificial Sequence
<220> FEATURE:
<223> OTHER INFORMATION: TMOF peptide

<400> SEQUENCE: 11

Tyr Asp Pro Ala Pro
1 5

<210> SEQ ID NO 12
<211> LENGTH: 6
<212> TYPE: PRT
<213> ORGANISM: Artificial Sequence
<220> FEATURE:
<223> OTHER INFORMATION: TMOF peptide

<400> SEQUENCE: 12

Tyr Asp Pro Ala Pro Pro
1 5

<210> SEQ ID NO 13
<211> LENGTH: 7
<212> TYPE: PRT
<213> ORGANISM: Artificial Sequence
<220> FEATURE:
<223> OTHER INFORMATION: TMOF peptide

<400> SEQUENCE: 13

Tyr Asp Pro Ala Pro Pro Pro
1 5

<210> SEQ ID NO 14
<211> LENGTH: 8
<212> TYPE: PRT
<213> ORGANISM: Artificial Sequence
<220> FEATURE:
<223> OTHER INFORMATION: TMOF peptide

<400> SEQUENCE: 14

Tyr Asp Pro Ala Pro Pro Pro Pro
1 5

<210> SEQ ID NO 15
<211> LENGTH: 6
<212> TYPE: PRT
<213> ORGANISM: Artificial Sequence
<220> FEATURE:
<223> OTHER INFORMATION: TMOF peptide

<400> SEQUENCE: 15

Asn Pro Thr Asn Leu His
1 5

<210> SEQ ID NO 16
<211> LENGTH: 2
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Can be Ala, Asp, Phe, Met, or Tyr.
<220> FEATURE:
<221> NAME/KEY: MISC_FEATURE -continued
<222> LOCATION: (2)..(2)
<223> OTHER INFORMATION: Can be Ala, Asp, Glu, Pro, or Tyr.

<400> SEQUENCE: 16

Xaa Xaa
1

<210> SEQ ID NO 17
<211> LENGTH: 3
<212> TYPE: PRT
<213> ORGANISM: Artificial Sequence
<220> FEATURE:
<223> OTHER INFORMATION: TMOF peptide

<400> SEQUENCE: 17

Ala Ala Pro
1

<210> SEQ ID NO 18
<211> LENGTH: 3
<212> TYPE: PRT
<213> ORGANISM: Artificial Sequence
<220> FEATURE:
<223> OTHER INFORMATION: TMOF peptide

<400> SEQUENCE: 18

Ala Asp Pro
1

<210> SEQ ID NO 19
<211> LENGTH: 5
<212> TYPE: PRT
<213> ORGANISM: Artificial Sequence
<220> FEATURE:
<223> OTHER INFORMATION: TMOF peptide

<400> SEQUENCE: 19

Ala Asp Pro Ala Pro
1               5

<210> SEQ ID NO 20
<211> LENGTH: 3
<212> TYPE: PRT
<213> ORGANISM: Artificial Sequence
<220> FEATURE:
<223> OTHER INFORMATION: TMOF peptide

<400> SEQUENCE: 20

Ala Pro Ala
1

<210> SEQ ID NO 21
<211> LENGTH: 3
<212> TYPE: PRT
<213> ORGANISM: Artificial Sequence
<220> FEATURE:
<223> OTHER INFORMATION: TMOF peptide

<400> SEQUENCE: 21

Asp Ala Ala
1

<210> SEQ ID NO 22
<211> LENGTH: 3
<212> TYPE: PRT
<213> ORGANISM: Artificial Sequence
<220> FEATURE:

-continued

<223> OTHER INFORMATION: TMOF peptide

<400> SEQUENCE: 22

Asp Pro Ala
1

<210> SEQ ID NO 23
<211> LENGTH: 2
<212> TYPE: PRT
<213> ORGANISM: Artificial Sequence
<220> FEATURE:
<223> OTHER INFORMATION: TMOF peptide

<400> SEQUENCE: 23

Asp Tyr
1

<210> SEQ ID NO 24
<211> LENGTH: 3
<212> TYPE: PRT
<213> ORGANISM: Artificial Sequence
<220> FEATURE:
<223> OTHER INFORMATION: TMOF peptide

<400> SEQUENCE: 24

Asp Tyr Pro
1

<210> SEQ ID NO 25
<211> LENGTH: 3
<212> TYPE: PRT
<213> ORGANISM: Artificial Sequence
<220> FEATURE:
<223> OTHER INFORMATION: TMOF peptide

<400> SEQUENCE: 25

Phe Ala Pro
1

<210> SEQ ID NO 26
<211> LENGTH: 3
<212> TYPE: PRT
<213> ORGANISM: Artificial Sequence
<220> FEATURE:
<223> OTHER INFORMATION: TMOF peptide

<400> SEQUENCE: 26

Phe Asp Pro
1

<210> SEQ ID NO 27
<211> LENGTH: 5
<212> TYPE: PRT
<213> ORGANISM: Artificial Sequence
<220> FEATURE:
<223> OTHER INFORMATION: TMOF peptide

<400> SEQUENCE: 27

Phe Asp Pro Ala Pro
1               5

<210> SEQ ID NO 28
<211> LENGTH: 3
<212> TYPE: PRT
<213> ORGANISM: Artificial Sequence
<220> FEATURE:
<223> OTHER INFORMATION: TMOF peptide -continued

<400> SEQUENCE: 28

Phe Ser Pro
1

<210> SEQ ID NO 29
<211> LENGTH: 9
<212> TYPE: PRT
<213> ORGANISM: Artificial Sequence
<220> FEATURE:
<223> OTHER INFORMATION: TMOF peptide

<400> SEQUENCE: 29

Met Pro Asp Tyr Pro Pro Pro Pro Pro
1 5

<210> SEQ ID NO 30
<211> LENGTH: 3
<212> TYPE: PRT
<213> ORGANISM: Artificial Sequence
<220> FEATURE:
<223> OTHER INFORMATION: TMOF peptide

<400> SEQUENCE: 30

Pro Ala Ala
1

<210> SEQ ID NO 31
<211> LENGTH: 3
<212> TYPE: PRT
<213> ORGANISM: Artificial Sequence
<220> FEATURE:
<223> OTHER INFORMATION: TMOF peptide

<400> SEQUENCE: 31

Pro Ala Pro
1

<210> SEQ ID NO 32
<211> LENGTH: 3
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (2)..(2)
<223> OTHER INFORMATION: Dextrorotary Asp

<400> SEQUENCE: 32

Tyr Xaa Pro
1

<210> SEQ ID NO 33
<211> LENGTH: 5
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (2)..(2)
<223> OTHER INFORMATION: Dextrorotary Asp

<400> SEQUENCE: 33

Tyr Xaa Pro Ala Pro
1 5

-continued

<210> SEQ ID NO 34
<211> LENGTH: 3
<212> TYPE: PRT
<213> ORGANISM: Artificial Sequence
<220> FEATURE:
<223> OTHER INFORMATION: TMOF peptide

<400> SEQUENCE: 34

Tyr Ala Pro
1

<210> SEQ ID NO 35
<211> LENGTH: 2
<212> TYPE: PRT
<213> ORGANISM: Artificial Sequence
<220> FEATURE:
<223> OTHER INFORMATION: TMOF peptide

<400> SEQUENCE: 35

Tyr Asp
1

<210> SEQ ID NO 36
<211> LENGTH: 3
<212> TYPE: PRT
<213> ORGANISM: Artificial Sequence
<220> FEATURE:
<223> OTHER INFORMATION: TMOF peptide

<400> SEQUENCE: 36

Tyr Asp Ala
1

<210> SEQ ID NO 37
<211> LENGTH: 5
<212> TYPE: PRT
<213> ORGANISM: Artificial Sequence
<220> FEATURE:
<223> OTHER INFORMATION: TMOF peptide

<400> SEQUENCE: 37

Tyr Asp Ala Ala Pro
1               5

<210> SEQ ID NO 38
<211> LENGTH: 3
<212> TYPE: PRT
<213> ORGANISM: Artificial Sequence
<220> FEATURE:
<223> OTHER INFORMATION: TMOF peptide

<400> SEQUENCE: 38

Tyr Asp Phe
1

<210> SEQ ID NO 39
<211> LENGTH: 5
<212> TYPE: PRT
<213> ORGANISM: Artificial Sequence
<220> FEATURE:
<223> OTHER INFORMATION: TMOF peptide

<400> SEQUENCE: 39

Tyr Asp Phe Ala Pro
1               5

-continued

<210> SEQ ID NO 40
<211> LENGTH: 3
<212> TYPE: PRT
<213> ORGANISM: Artificial Sequence
<220> FEATURE:
<223> OTHER INFORMATION: TMOF peptide

<400> SEQUENCE: 40

Tyr Asp Gly
1

<210> SEQ ID NO 41
<211> LENGTH: 5
<212> TYPE: PRT
<213> ORGANISM: Artificial Sequence
<220> FEATURE:
<223> OTHER INFORMATION: TMOF peptide

<400> SEQUENCE: 41

Tyr Asp Leu Ala Pro
1 5

<210> SEQ ID NO 42
<211> LENGTH: 3
<212> TYPE: PRT
<213> ORGANISM: Artificial Sequence
<220> FEATURE:
<223> OTHER INFORMATION: TMOF peptide

<400> SEQUENCE: 42

Tyr Asp Pro
1

<210> SEQ ID NO 43
<211> LENGTH: 3
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Dextrorotary Tyr

<400> SEQUENCE: 43

Xaa Asp Pro
1

<210> SEQ ID NO 44
<211> LENGTH: 5
<212> TYPE: PRT
<213> ORGANISM: Artificial Sequence
<220> FEATURE:
<223> OTHER INFORMATION: TMOF peptide

<400> SEQUENCE: 44

Tyr Asp Pro Ala Phe
1 5

<210> SEQ ID NO 45
<211> LENGTH: 5
<212> TYPE: PRT
<213> ORGANISM: Artificial Sequence
<220> FEATURE:
<223> OTHER INFORMATION: TMOF peptide

<400> SEQUENCE: 45

Tyr Asp Pro Ala Leu

-continued 1 5

<210> SEQ ID NO 46
<211> LENGTH: 5
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Dextrorotary Tyr

<400> SEQUENCE: 46

Xaa Asp Pro Ala Pro
1 5

<210> SEQ ID NO 47
<211> LENGTH: 5
<212> TYPE: PRT
<213> ORGANISM: Artificial Sequence
<220> FEATURE:
<223> OTHER INFORMATION: TMOF peptide

<400> SEQUENCE: 47

Tyr Asp Pro Phe Pro
1 5

<210> SEQ ID NO 48
<211> LENGTH: 5
<212> TYPE: PRT
<213> ORGANISM: Artificial Sequence
<220> FEATURE:
<223> OTHER INFORMATION: TMOF peptide

<400> SEQUENCE: 48

Tyr Asp Pro Gly Pro
1 5

<210> SEQ ID NO 49
<211> LENGTH: 5
<212> TYPE: PRT
<213> ORGANISM: Artificial Sequence
<220> FEATURE:
<223> OTHER INFORMATION: TMOF peptide

<400> SEQUENCE: 49

Tyr Asp Pro Leu Pro
1 5

<210> SEQ ID NO 50
<211> LENGTH: 5
<212> TYPE: PRT
<213> ORGANISM: Artificial Sequence
<220> FEATURE:
<223> OTHER INFORMATION: TMOF peptide

<400> SEQUENCE: 50

Tyr Glu Pro Ala Pro
1 5

<210> SEQ ID NO 51
<211> LENGTH: 5
<212> TYPE: PRT
<213> ORGANISM: Artificial Sequence
<220> FEATURE:
<223> OTHER INFORMATION: TMOF peptide -continued

<400> SEQUENCE: 51

Tyr Phe Pro Ala Pro
1 5

<210> SEQ ID NO 52
<211> LENGTH: 5
<212> TYPE: PRT
<213> ORGANISM: Artificial Sequence
<220> FEATURE:
<223> OTHER INFORMATION: TMOF peptide

<400> SEQUENCE: 52

Tyr Asn Pro Ala Pro
1 5

<210> SEQ ID NO 53
<211> LENGTH: 3
<212> TYPE: PRT
<213> ORGANISM: Artificial Sequence
<220> FEATURE:
<223> OTHER INFORMATION: TMOF peptide

<400> SEQUENCE: 53

Tyr Ser Phe
1

<210> SEQ ID NO 54
<211> LENGTH: 5
<212> TYPE: PRT
<213> ORGANISM: Artificial Sequence
<220> FEATURE:
<223> OTHER INFORMATION: TMOF peptide

<400> SEQUENCE: 54

Tyr Ala Pro Ala Pro
1 5

<210> SEQ ID NO 55
<211> LENGTH: 5
<212> TYPE: PRT
<213> ORGANISM: Artificial Sequence
<220> FEATURE:
<223> OTHER INFORMATION: TMOF peptide

<400> SEQUENCE: 55

Tyr Ser Pro Ala Pro
1 5

<210> SEQ ID NO 56
<211> LENGTH: 5
<212> TYPE: PRT
<213> ORGANISM: Artificial Sequence
<220> FEATURE:
<223> OTHER INFORMATION: TMOF peptide

<400> SEQUENCE: 56

Tyr Asp Pro Ala Ala
1 5

<210> SEQ ID NO 57
<211> LENGTH: 4
<212> TYPE: PRT
<213> ORGANISM: Artificial Sequence
<220> FEATURE:
<223> OTHER INFORMATION: TMOF peptide

<400> SEQUENCE: 57

-continued

Tyr Asp Pro Ala
1

<210> SEQ ID NO 58
<211> LENGTH: 2
<212> TYPE: PRT
<213> ORGANISM: Artificial Sequence
<220> FEATURE:
<223> OTHER INFORMATION: TMOF peptide

<400> SEQUENCE: 58

Ala Asp
1

<210> SEQ ID NO 59
<211> LENGTH: 10
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Can be Ala, Asp, or Tyr.
<220> FEATURE:
<221> NAME/KEY: MISC_FEATURE
<222> LOCATION: (2)..(2)
<223> OTHER INFORMATION: Can be Ala, Asp, or Ser.
<220> FEATURE:
<221> NAME/KEY: MISC_FEATURE
<222> LOCATION: (3)..(3)
<223> OTHER INFORMATION: Can be Phe or Pro.
<220> FEATURE:
<221> NAME/KEY: MISC_FEATURE
<222> LOCATION: (4)..(4)
<223> OTHER INFORMATION: Is optionally present and can be Phe or Gly.
<220> FEATURE:
<221> NAME/KEY: MISC_FEATURE
<222> LOCATION: (5)..(5)
<223> OTHER INFORMATION: Is optionally present and can be Phe, Leu, or Pro.
<220> FEATURE:
<221> NAME/KEY: MISC_FEATURE
<222> LOCATION: (6)..(10)
<223> OTHER INFORMATION: Each of amino acids 6-10 are optionally present.

<400> SEQUENCE: 59

Xaa Xaa Xaa Xaa Xaa Pro Pro Pro Pro Pro
1               5                   10

<210> SEQ ID NO 60
<211> LENGTH: 10
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Can be Ala, Asp, or Tyr.
<220> FEATURE:
<221> NAME/KEY: MISC_FEATURE
<222> LOCATION: (2)..(2)
<223> OTHER INFORMATION: Can be Ala, Pro, or Ser.
<220> FEATURE:
<221> NAME/KEY: MISC_FEATURE
<222> LOCATION: (3)..(3)
<223> OTHER INFORMATION: Can be Ala, Phe, or Pro.
<220> FEATURE:
<221> NAME/KEY: MISC_FEATURE
<222> LOCATION: (4)..(4)
<223> OTHER INFORMATION: Is optionally present and can be Ala, -continued

```
     Phe, or Gly.
<220> FEATURE:
<221> NAME/KEY: MISC_FEATURE
<222> LOCATION: (5)..(5)
<223> OTHER INFORMATION: Is optionally present and can be Phe,
     Leu, or Pro.
<220> FEATURE:
<221> NAME/KEY: MISC_FEATURE
<222> LOCATION: (6)..(10)
<223> OTHER INFORMATION: Each of amino acids 6-10 are optionally
     present.

<400> SEQUENCE: 60

Xaa Xaa Xaa Xaa Xaa Pro Pro Pro Pro Pro
1               5                   10
```

PESTICIDAL PEPTIDES

BACKGROUND OF THE INVENTION

Many blood-ingesting pests are known to feed on humans and animals, and many pests are vectors for pathogenic microorganisms which threaten human and animal health, including commercially important livestock, pets and other animals. Various species of mosquitoes, for example, transmit diseases caused by viruses, and many are vectors for disease-causing nematodes and protozoa. Mosquitoes of the genus Anopheles transmit Plasmodium, the protozoan which causes malaria, a devastating disease which results in approximately 1 million deaths annually. The mosquito species *Aedes aegypti* transmits an arbovirus that causes yellow fever in humans. Other arboviruses transmitted by Aedes species include the causative agents of dengue fever, eastern and western encephalitis, Venezuelan equine encephalitis, St. Louis encephalitis, chikungunya, oroponehe and bunyarnidera. The genus Culex, which includes the common house mosquito *C. pipiens*, is implicated in the transmission of various forms of encephalitis and filarial worms. The common house mosquito also transmits *Wuchereria bancrofti* and *Brugia malayi*, which cause various forms of lymphatic filariasis, including elephantiasis. *Trypanasomacruzi*, the causative agent of Chagas' disease, is transmitted by various species of blood-ingesting Triatominae bugs. The tsetse fly (Glossina spp.) transmits African trypanosomal diseases of humans and cattle. Many other diseases are transmitted by various blood-ingesting pest species. The order Diptera contains a large number of blood-ingesting and disease-bearing pests, including, for example, mosquitoes, black flies, no-see-ums (punkies), horse flies, deer flies and tsetse flies.

Various pesticides have been employed in efforts to control or eradicate populations of disease-bearing pests, such as disease-bearing blood-ingesting pests. For example, DDT, a chlorinated hydrocarbon, has been used in attempts to eradicate malaria-bearing mosquitoes throughout the world. Other examples of chlorinated hydrocarbons are BHC, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-pest organisms.

Another common class of pesticides is the organophosphates, which is perhaps the largest and most versatile class of pesticides. Organophosphates include, for example, parathion, Malathion™, diazinon, naled, methyl parathion, and dichlorvos. Organophosphates are generally much more toxic than the chlorinated hydrocarbons. Their pesticidal effect results from their ability to inhibit the enzyme cholinesterase, an essential enzyme in the functioning of the insect nervous system. However, they also have toxic effects on many animals, including humans.

The carbamates, a relatively new group of pesticides, include such compounds as carbamyl, methomyl, and carbofuran. These compounds are rapidly detoxified and eliminated from animal tissues. Their toxicity is thought to involve a mechanism similar to the mechanism of the organophosphates; consequently, they exhibit similar shortcomings, including animal toxicity.

A major problem in pest control results from the capability of many species to develop pesticide resistance. Resistance results from the selection of naturally-occurring mutants possessing biochemical, physiological or behavioristic factors that enable the pests to tolerate the pesticide.

Species of Anopheles mosquitoes, for example, have been known to develop resistance to DDT and dieldrin. DDT substitutes, such as Malathion™, propoxur and fenitrothion are available; however, the cost of these substitutes is much greater than the cost of DDT.

There is clearly a longstanding need in the art for pesticidal compounds that are pest-specific, that reduce or eliminate direct and/or indirect threats to human health posed by presently available pesticides, that are environmentally compatible in the sense that they are biodegradable, and are not toxic to non-pest organisms, and have reduced or no tendency to bioaccummulate.

Many pests, including for example blood-inbibing pests, must consume and digest a proteinaceous meal to acquire sufficient essential amino acids for growth, development and the production of mature eggs. Adult pests, such as adult mosquitoes, need these essential amino acids for the production of vitellogenins by the fat body. These vitellogenins are precursors to yolk proteins which are critical components of oogenesis. Many pests, such as house flies and mosquitoes, produce oostatic hormones that inhibit egg development by inhibiting digestion of the protein meal, and thereby limiting the availability of the essential amino acids necessary for egg development.

Serine esterases such as trypsin and trypsin-like enzymes (collectively referred to herein as "TTLE") are important components of the digestion of proteins by insects. In the mosquito, *Aedes aegypti*, an early trypsin that is found in the midgut of newly emerged females is replaced, following the blood meal, by a late trypsin. A female mosquito typically weighs about 2 mg and produces 4 to 6 μg of trypsin within several hours after a ingesting blood meal. Continuous boisynthesis at this rate would exhaust the available metabolic energy of a female mosquito; as a result, the mosquito would be unable to produce mature eggs, or even to find an oviposition site. To conserve metabolic energy, the mosquito regulates TTLE biosynthesis with a peptide hormone named Trypsin Modulating Oostatic Factor (TMOF). TMOF mosquitoes produce in the follicular epithelium of the ovary 12–35 hours after a blood meal; TMOF is then released into the hemolymph where it binds to a specific receptor on the midgut epithelial cells, signaling the termination of TTLE biosynthesis.

This regulatory mechanism is not unique for mosquitoes; flesh flies, fleas, sand flies, house flies, dog flies and other insect pests which need protein as part of their diet have similar regulatory mechanisms.

In 1985, Borovsky purified an oostatic hormone 7,000-fold and disclosed that injection of a hormone preparation into the body cavity of blood imbibed mosquitoes caused inhibition of egg development and sterility (Borovsky, D. [1985] *Arch. Insect Biochem. Physiol.* 2:333–349). Following these observations, Borovsky (Borovsky, D. [1988] *Arch. Ins. Biochem. Physiol.* 7:187–210) reported that injection or passage of a peptide hormone reparation into mosquitoes inhibited the TTLE biosynthesis in the epithelial cells of the gut. This inhibition caused inefficient digestion of the blood meal and a reduction in the availability of essential amino acids translocated by the hemolymph, resulting in arrested egg development in the treated insect. Borovsky observed that this inhibition of egg development does not occur when the oostatic hormone peptides are inside the lumen of the gut or other parts of the digestive system (Borovsky, D. [1988], supra).

Following the 1985 report, the isolated hormone, (a ten amino acid peptide) and two TMOF analogues were disclosed in U.S. Pat. No. 5,011,909 and 5,130,253, and in a 1990 publication (Borovsky et al. [1990]*FASEB J.* 4:3015–3020).Additionally, U.S. Pat. No. 5,358,934 discloses truncated forms of the full length TMOF which have prolines removed from the carboxy terminus, including the peptides YDPAP, YDPAPP, YDPAPPP, and YDPAPPPP.

Neuropeptides Y (NPY) are an abundant family of peptides that are widely distributed in the central nervous system of vertebrates. NPY peptides have also been recently isolated and identified in a cestode, a turbellarian, and in terrestrial and marine molluscs (Maule et al., 1991 "Neuropeptide F: A Novel Parasitic Flatworm Regulatory Peptide from *Moniezia expansa* (Cestoda: Cyclophylidea)" Parasitology 102:309–316; Curry et al., 1992 "Neuropeptide F: Primary Structure from the Turbellarian, *Arthioposthia triangulata*" Comp. Biochem. Physiol. 101C:269–274; Leung et al., 1992 "The Primary Structure of Neuropeptide F (NPF) from the Garden Snail, *Helix aspersa*" Regul. Pep. 41:71–81; Rajpara et al., 1992 "Identification and Molecular Cloning of Neuropeptide Y Homolog that Produces Prolonged Inhibition in Aplysia Neurons" Neuron. 9:505–513).

Invertebrate NPYs are highly homologous to vertebrate NPYs. The major difference between vertebrate and invertebrate NPYs occurs at the C-terminus where the vertebrate NPY has an amidated tyrosine (Y) whereas invertebrates have an amidated phenylalanine (F). Because of this difference, the invertebrate peptides are referred to as NPF peptides.

Cytoimmunochemical analyses of NPY peptides suggest that they are concentrated in the brain of various insects, including the Colorado potato beetle *Leptinotarsa decemlineata* (Verhaert et al., 1985 "Distinct Localization of FMRF amide- and Bovine Pancreatic Polypeptide-Like Material in the Brain, Retrocerebal Complex and Subesophageal Ganglion of the Cockroach *Periplaneta americana*" L. Brain Res. 348:331–338; Veenstra et al., 1985 "Immunocytochemical Localization of Peptidergic Neurons and Neurosecretory Cells in the Neuro-Endocrine System of the Colorado Potato Beetle with Antisera to Vertebrate Regulatory Peptides" Histochemistry 82:9–18). Partial purification of NPY peptides in insects suggests that both NPY and NPF are synthesized in insects (Duve et al., 1981 "Isolation and Partial Characterization of Pancreatic Polypeptide-like Material in the Brain of the Blowfly *Alliphora vomitoria*" Biochem. J. 197, 767–770).

Researchers have recently isolated two neuropeptides with NPF-like immunoreactivity from brain extracts of the Colorado potato beetle. The researchers purified the peptides using $C_{18}$ reversed phase high pressure liquid chromatography (HPLC), and determined their structure using mass spectrometry. The deduced structures of these peptides are: Ala-Arg-Gly-Pro-Gln-Leu-Arg-Leu-Arg-Phe-amid (SEQ ID NO. 1) and Ala-Pro-Ser-Arg-Leu-Arg-Phe-amide (SEQ ID NO. 2) designated NPF I and NPF II, respectively (Spittaels, Kurt, Peter Verhaert, Chris Shaw, Richard N. Johnston et al. [1996] *Insect Biochem. Molec. Biol.* 26(4) :375–382).

BRIEF SUMMARY OF THE INVENTION

The subject invention concerns novel pesticidal polypeptides and other compounds. In a preferred embodiment, the pesticidal agents of the subject invention (collectively referred to herein as "pesticidal compounds") inhibit digestion in pests by terminating or otherwise blocking synthesis of digestive enzymes by activating a TMOF receptor. The pesticidal polypeptides and other compounds of the present invention are usefully employed in the control of pests, such as mosquitoes, which ingest blood.

In one aspect, the pesticidal compounds of the present invention comprise novel polypeptides comprising an amino acid sequence having the formula:

$$A^1A^2A^3A^4A^5F \quad \text{(Formula I)}$$

wherein:

- $A^1$ is selected from the group consisting of Y, A, D, F, G, M, P, S, and Y;
- $A^2$ is selected from the group consisting of A, D, E, F, G, N, P, S, and Y;
- $A^3$ is optionally present and is selected from the group consisting of A, D, F, G, L, P, S, and Y;
- $A^4$ is optionally present when $A^3$ is present and is selected from the group consisting of A, F, G, L, and Y;
- $A^5$ is optionally present when $A^4$ is present and is selected from the group consisting of A, F, L, and P;
- F is a flanking region which is optionally present and is selected from the group consisting of P, PP, PPP, PPPP, and PPPPP.

The pesticidal compound preferably does not consist of $YDPAP_6$, $DYPAP_6$, $PAP_6$, YDPAP, $YDPAP_2$, $YDPAP_3$, $YDPAP_4$, NPTNLH, or DF-OMe.

In a narrower aspect, the pesticidal compound comprises a polypeptide having an amino acid sequence which consists essentially of the amino acid sequence of Formula I. In a preferred aspect, where the amino acid sequence is a TMOF fragment, the pesticidal compound lacks TMOF amino acids adjacent to the TMOF fragment. Instill another aspect, the peptide consists of the amino acid sequence of Formula I.

In another aspect, only $A^1$, $A^2$, $A^3$, $A^4$, and F of Formula I are present and F is attached to $A^4$. In yet another aspect, only $A^1$, $A^2$, $A^3$, and $A^4$ of Formula I are present. In still a further aspect, only $A^1$, $A^2$, $A^3$, and F of Formula I are present and F is attached to $A^4$. In an additional aspect, only $A^1$, $A^2$, and $A^3$ of Formula I are present. In another aspect, only $A^1$, $A^2$, and F of Formula I are present and F is attached to $A^2$, and in a further aspect, only $A^1$ and $A^2$ of Formula I are present. In a preferred mode, A and D are present in the amino acid sequence and, more preferably, A, D, and Y are present.

One embodiment of the subject invention concerns a peptide comprising an amino acid sequence having the formula $A^1A^2$ (Formula II), wherein $A^1$ is an amino acid residue selected from the group consisting of A, D, F, M, and Y, and $A^2$ is an amino acid residue selected from the group consisting of A, D, E, P, and Y. In a preferred embodiment, the subject invention is directed to peptides which comprise the amino acids A, D, and Y.

The pesticidal compounds of the present invention have advantageous biological activity against pests. The novel polypeptides and other compounds of the invention are particularly active against blood-sucking insects, particularly against species of mosquitoes such as *Aedes aegypti* that are common vectors of arthropod-borne viral diseases, such as arboviruses. Other biting pests such as flies, fleas, ticks, and lice can also be controlled using peptides and methods of the subject invention. These pests utilize as their primary blood-digesting enzymes.

The subject peptides can also be used to control pests of agricultural crops. These pests include, for example, coleopterans (beetles), lepidopterans (caterpillars), and mites. The compounds of the subject invention can also be used to control household pests including, but not limited to, ants and cockroaches.

A further aspect of the subject invention are addition salts, complexes, or prodrugs such as esters of the peptides described herein, especially the nontoxic pharmaceutically or agriculturally acceptable acid addition salts. The acid addition salts can be prepared using standard procedures in a suitable solvent from the parent compound and an excess of an acid, such as hydrochloric, hydrobromic, sulfuric, phosphoric, acetic, maleic, succinic, ethanedisulfonic or methanesulfonic acids. Esterification to form derivatives such as the methyl or ethyl esters, can also be performed using standard procedures.

The N-terminus and C-terminus of the pesticidal polypeptides can be blocked to further inhibit proteolysis by metabolic enzymes. Derivation of peptides to block the N-terminus or C-terminus is known in the art. For example, the N-terminus can be acetylated by methods known to those of ordinary skill in the art, and/or the C-terminus can be amidated as is well known in the art.

Peptides containing the above sequences in which only conservative substitutions have been made are also provided by the present invention. Analogues of the above-mentioned proteins and peptides which have one or more amino acid substitutions forming a branched peptide (e.g., by substitution with an amino acid or amino acid analogue having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally, to provide a sulfhydryl group for disulfide bond formation), are also provided.

The pesticidal polypeptides and other compounds of the present invention may also comprise D-conformation amino acids which can inhibit the ability of proteases to degrade the polypeptides. Also, derivation of the pesticidal compounds with long chain hydrocarbons will facilitate passage through the cuticle into the pest body cavity. Therefore, in a further embodiment, the subject invention provides compositions comprising the pesticidal polypeptides bound to lipids or other carriers.

Yet another aspect of the subject invention pertains to DNA sequences encoding the pesticidal polypeptides disclosed herein. These DNA sequences can readily be synthesized by a person skilled in the art, and can be used to transform an appropriate prokaryotic or eukaryotic host to enable the host to express the novel peptides. Hosts of particular interest include bacteria, yeasts, viruses, and plants. Furthermore, viruses may also be modified to transmit polynucleotides encoding the pesticidal polypeptides of the present invention. For each of these hosts, the DNA sequences may be specifically designed by a person skilled in the art to utilize codons known to be optimally expressed in the particular hosts. Advantageous promoters can also easily be employed in the polynucleotide sequences. Bacteria, yeasts, plants, and viruses each may be used in the production of pesticidal polypeptides for further use, or these hosts can be used as vehicles for direct application of the pesticidal polypeptides to the target pest. Plants can be transformed to render them toxic to a target pest species which feeds on the transformed plant. Methods for transforming plant cells utilizing, for example, Agrobacteria, are well known to those skilled in the art.

Another aspect of the subject invention pertains to a method for controlling pests comprising administering to said pest an effective amount of a pesticidal polypeptide compound of the subject invention.

The subject invention provides pest control compositions comprising pesticidal compounds and a suitable pesticidal carrier. The pest control compositions are formulated for application to the target pests or their situs. In a specific embodiment, the present invention provides recombinant hosts transformed to express a pesticidal polypeptide. The recombinant host may be, for example, prokaryotic or eukaryotic cells such as yeast or algae which have been transformed to express a pesticidal compound of the subject invention. The transformed hosts can be applied to pest habitats, such as bodies of water inhibited by mosquito larvae. Ingestion of the transformed host by a pest species in control of the pest by the pesticidal polypeptide.

In a preferred embodiment for the control of agricultural pests, the subject invention provides transformed plants which express a pesticidal polypeptide. Pest control is achieved when the pest ingests the transformed plant material.

The methods and materials of the subject invention provide a novel approach to controlling insects and insect-transmitted diseases. The peptides of the subject invention have advantageous activity and increased resistance to proteolysis over previously disclosed compounds.

As used herein, the term "pesticidally effective" is used to indicate an amount or concentration of a pesticidal compound which is sufficient to reduce the number of pests in a geographical locus as compared to a corresponding geographical locus in the absence of the amount or concentration of the pesticidal compound.

The term "pesticidal" is not intended to refer only to the ability to kill pests, but also includes the ability to interfere with a pest's life cycle in any way that results in an overall reduction in the pest population. For example, the term "pesticidal" includes inhibition of a pest from progressing from one form to a more mature form, e.g., transition between various larval instars or transition from larva to pupa or pupa to adult. Further, the term "pesticidal" is intended to encompass anti-pest activity during all phases of a pest's life cycle; thus, for example, the term includes larvacidal, ovicidal , and adulticidal activity.

The word "transform" is broadly used herein to refer to introduction of an exogenous polynucleotide sequence into a prokaryotic or eukaryotic cell by any means known in the art (including for example, direct transmission of a polynucleotide sequence from a cell or virus particle, transmission by infective virus particles and transmission by any other nucleotide-bearing construct) resulting in a permanent or temporary alteration of genotype and in an immortal or non-immortal cell.

The terms "polypeptide,""peptide," and "protein" as used herein are intended to refer to amino acid sequences of any length.

BRIEF DESCRIPTION OF THE SEQUENCES

SEQ ID NO. 1 is the amino acid sequence for TMOF.

SEQ ID NOS. 2–42 are TMOF peptide analogs according to the subject invention.

SEQ ID NOS. 43–44 are TMOF receptors according to the subject invention.

DETAILED DESCRIPTION OF THE INVENTION

The subject invention concerns novel pest control compounds and methods for using such compounds. Specifically exemplified are novel pesticidal polypeptides, compositions comprising said pesticidal polypeptides and the use of such pesticidal polypeptides and compositions in controlling pests, such as mosquitoes.

In one aspect, the biological control agents comprise novel polypeptides, comprising an amino acid sequence of the formula:

$$A^1A^2A^3A^4A^5F \quad \text{(Formula I)}$$

wherein:

$A^1$ is selected from the group consisting of Y, A, D, F, G, M, P, S, and Y;

$A^2$ is selected from the group consisting of A, D, E, F, G, N, P, S, and Y;

$A^3$ is optionally present and is selected from the group consisting of A, D, F, G, L, P, S, and Y;

$A^4$ is optionally present when $A^3$ is present and is selected from the group consisting of A, F, G, L, and Y;

$A^5$ is optionally present when $A^4$ is present and is selected from the group consisting of A, F, L, and P;

F is a flanking region which is optionally present and is selected from the group consisting of P, PP, PPP, PPPP, and PPPPP.

The peptide preferably does not consist of $YDPAP_6$, $DYPAP_6$, $PAP_6$, YDPAP, $YDPAP_2$, $YDPAP_3$, $YDPAP_4$, NPTNLH, or DF-OMe.

In a narrower aspect the polypeptide comprises an amino acid sequence which consists essentially of the amino acid sequence of Formula I. In a preferred aspect, where the amino acid sequence is a TMOF fragment, the peptide or protein lacks TMOF amino acids adjacent to the TMOF fragment. In still another aspect, the pesticidal polypeptide consists of the amino acid sequence of Formula I.

In another aspect, only $A^1$, $A^2$, $A^3$, $A^4$, and F of Formula I are present and F is attached to $A^4$. In yet another aspect, only $A^1$, $A^2$, $A^3$, and $A^4$ of Formula I are present. In an additional aspect, only $A^1$, $A^2$, $A^3$ and F of Formula I are present and F is attached to $A^3$. In another aspect, only $A^1$, $A^2$, and $A^3$ of Formula I are present. In another aspect, only $A^1$, $A^2$, and F of Formula I are present,. and F is attached to $A^2$. In a further aspect, only $A^1$ and $A^2$ of Formula I are present. In a preferred mode, A and D are present in the amino acid sequence and, more preferably, A, D, and Y are present.

One embodiment of the subject invention concerns a peptide having the formula $A^1A^2$ (Formula II) wherein $A^1$ is an amino acid selected from the group consisting of A, D, F, M, and Y, and $A^2$ is an amino acid selected from the group consisting of A, D, E, P, and Y. In a preferred embodiment, the subject invention is directed to peptides which comprise the amino acids A, D, and Y.

In a preferred mode, the pesticidal polypeptides of the present invention comprise truncated forms of TMOF having 50% or fewer amino acids than the corresponding TMOF. Preferably the truncated forms have 2–10 amino acid residues. More preferably the truncated forms have 2–8 amino acid residues. Most preferably, the truncated forms have 2–5 amino acid residues. Despite this substantial truncation, the pesticidal polypeptides retain some or all of the biological activity of the full-length peptide. Further, the pesticidal polypeptides of the subject invention are particularly advantageous because of more rapid and efficient penetration into the midgut, and are less expensive to produce by conventional chemical methods.

Preferably, the subject peptides have an $LD_{50}$ against mosquito larvae of less than 3.0 $\mu$mole/ml. More preferably, the peptides have an $LD_{50}$ of less than 2.0 pmole/ml, and, most preferably, the peptides have an $LD_{50}$ of less than 1.0 $\mu$mole/ml. As used herein, "$LD_{50}$" refers to a lethal dose of a peptide able to cause 50% mortality of larvae maintained on a diet of 1 mg/ml autoclaved yeast supplemented with the pesticidal polypeptide. (Borovsky, Dov, and Farida Mahmood [1995] *Regulatory Peptides* 57:273–281).

The one-letter symbol for the amino acids used herein is well known in the art. For convenience, the relationship of the three-letter abbreviation and the one-letter symbol for amino acids is as follows:

| | | | |
|---|---|---|---|
| Ala | A | Leu | L |
| Arg | R | Lys | K |
| Asn | N | Met | M |
| Asp | D | Phe | F |
| Cys | C | Pro | P |
| Gln | Q | Ser | S |
| Glu | E | Thr | T |
| Gly | G | Trp | W |
| His | H | Tyr | Y |
| Ile | I | Val | V |

The pesticidal polypeptides of the present invention may be provided as a fusion polypeptide, the amino acid sequence of which includes one or more pesticidal polypeptides of the present invention, and optionally comprises one ore more heterologous polypeptides. In various specific embodiments, two or more of the pesticidal polypeptides are linked, for example, by peptide bonds between the N-terminus of one portion and the C-terminus of another portion. In other aspects, one or more of the pesticidal polypeptides can be linked to one or more heterologous peptides or proteins to form pesticidal fusion polypeptides. Molecules comprising such portions linked by hydrocarbon linkages are also provided. Derivatives of the foregoing fusion proteins are also provided (e.g., branched, cyclized, or C-terminal chemically modified, etc.). Further, two or more peptides of the general Formulas I and/or II can be linked to each other.

Pesticidal polypeptides comprising the sequences of Formulas I and/or II in which only conservative substitutions have been made are also provided by the present invention. Analogues which have one or more amino acid substitutions forming a branched peptide (e.g., by substitution with an amino acid or amino acid analogue having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally, to provide a sulfhydryl group for disulfide bond formation), are also provided.

Nonclassical amino acids and/or chemical amino acid analogues can be introduced as a substitution for an existing amino acid residue, or as an insertion into the amino acid sequence of the pesticidal polypeptides of the present invention, or as an addition to a terminus of the pesticidal polypeptides. Non-classical amino acids include but are not limited to the D-isomers of the common amino acids, 2,4-diaminobutyric acid, $\alpha$-amino isobutyric acid, 4-aminobutyric acid, Abu, 2-amino butyric acid, $\gamma$-Abu, $\epsilon$-Ahx, 6-amino hexanoic acid, Aib, 2-amino isobutyric acid, 3-amino propionic acid, omithine, norleucine, norvaline, hydroxyproline, sarcosine, citruline, homocitrulline, cysteic acid, t-butylglycine, t-butylalanine, phenylglycine, cyclohexylalanine, $\beta$-alanine, fluoro-amino acids, designer amino acids such as $\beta$-methyl amino acids, C-methyl amino acids, N-methyl amino acids, and amino acid analogues in general. Furthermore, the amino acid can be D (dextrorotary) or L (levorotary). Dextrorotary amino acids are indicated herein by a parenthetical D, i.e., "(D)", immediately preceding the dextrorotary amino acid.

Thus, the pesticidal polypeptide derivatives include peptides containing as a primary amino acid sequence all or part of the peptide sequence of Formulas I and/or II, including altered sequences in which functionally equivalent amino acid residues are substituted for residues within the sequence, resulting in a peptide which is functionally active. For example, one or more amino acid residues within the sequence can be substituted by another amino acid of a similar polarity, which acts as a functional equivalent, resulting in a silent alteration. Conservative substitutions for an amino acid within the sequence may be selected from other members of the class to which the amino acid belongs (see Table 1). Such pesticidal polypeptide derivatives can be made either by chemical peptide synthesis or by recombinant production from polynucleotide sequences encoding the pesticidal polypeptide. The subject invention further includes other pesticidal compounds which bind to a TMOF receptor. As used herein, "TMOF compounds" refers to pesticidal polypeptides of Formulas I and II as well as other polypeptides and compounds which bind to a TMOF receptor as described herein.

TMOF receptors and polynucleotides. In one embodiment, the subject invention is directed to the control of pests using a pesticidal compound which binds to or otherwise associates with a TMOF receptor. Specifically exemplified herein is a TMOF receptor comprising the amino acid sequence shown in SEQ ID NO. 44. Preferably, the polypeptide is encoded by a complete polynucleotide nucleotide sequence of a TMOF receptor gene, or a fragment analogue, derivative or other functional equivalent thereof which encodes polypeptides having TMOF receptor activity. In a specific embodiment, the TMOF receptor is encoded by a polynucleotide sequence comprising the coding sequence (nucleotides 1–186) shown in SEQ ID NO. 43 or other polynucleotide sequence with codons encoding the amino acid sequence of SEQ ID NO. 44.

Isolated TMOF receptors can be used to produce antibodies according to known techniques. These antibodies may be monoclonal or polyclonal. These antibodies can be used to screen an expression library to identify other clones expressing polypeptides having TMOF receptor activity. Alternatively, these antibodies may be used to identify TMOF receptors from their natural material such as mosquito gut material.

A specific TMOF receptor sequence is exemplified herein. This sequence is merely exemplary of TMOF receptors. Variant or equivalent receptors (and nucleotide sequences coding for equivalent receptors) having the same or similar TMOF receptor activity can also be utilized. Equivalent receptors will typically have amino acid homology with the exemplified receptor. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the receptor that account for biological activity or are involved in the determination of three-dimensional configuration, which ultimately is responsible for the biological activity. In this regard, certain amino acid substitutions are acceptable and can be expected if these substitutions are in regions that are not critical to biological activity or are conservative amino acid substitutions that do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not completely diminish the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not completely diminish the biological activity of the receptor.

The use of polynucleotide probes is well known to those skilled in the art. In one specific example, a cDNA library for mosquito gut cells can be created by routine means, and DNA of interest can be isolated therefrom. Polynucleotides of the subject invention can be used to hybridize with DNA fragments of the constructed cDNA-library, allowing identification of and selection (or "probing out") of the genes of interest, i.e., those nucleotide sequences which hybridize with the probes of the subject invention and encode polypeptides having TMOF receptor activity. The isolation of these genes can be performed by a person skilled in the art, having the benefit of the instant disclosure, using techniques which are well-known in the molecular biology art.

Thus, it is possible, without the aid of biological analysis, to identify polynucleotide sequences encoding TMOF receptors. Such a probe analysis provides a rapid method for identifying genes encoding TMOF receptors from a wide variety of hosts. The isolated genes can be inserted into appropriate vehicles which can then be used to transform a suitable host.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, NY., pp. 169–170.

Examples of various stringency conditions are provided herein. Hybridization of immobilized DNA on Southern blots with 32P-labeled gene-specific probes can be performed by standard methods (Maniatis et al. (1982) *Molecular Cloning: A Laboratory Manual*, Cold Spring Harbor Laboratory, New York.). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. et al. [1983] *Methods of Enzymology*, R. Wu, L. Grossman and K. Moldave [eds.] Academic Press, New York 100:266–285).

Tm=81.5° C.+16.6 Log[Na+]+0.41(%G+C)−0.61 (%formamide)−600/length of duplex in base pairs.

Washes are typically carried out as follows:

(1) twice at room temperature for 15 minutes in 1×SSPE, 0.1% SDS (low stringency wash);

(2) once at Tm-20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

Tm (° C.)=2(number T/A base pairs)+4(number G/C base pairs) (Suggs et al. [1981] ICN-UCLA *Symp. Dev. Biol. Using Purified Genes*, D. D. Brown [ed.], Academic Press, New York, 23:683–693).

Washes can be carried out as follows:

(1) twice at room temperature for 15 minutes 1×SSPE, 0.1% SDS (low stringency wash;

(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

Identification of pest control compounds. The TMOF receptors can advantageously be used to identify pesticidal compounds and/or confirm or characterize the activity of the pesticidal polypeptides of the subject invention. The pesticidal compounds of the subject invention are preferably those which bind to, or otherwise associate with, the TMOF receptor in a way which activates the TMOF receptor, thereby inhibiting biosynthesis of TTLE, resulting in control of the pest population. A person skilled in the art, having the benefit of the instant disclosure, can utilize the TMOF receptors described herein to identify and characterize pesticidal compounds of the subject invention. In one embodiment, the TMOF receptor can be purified from its natural sources using, for example, antibodies to the TMOF receptor to obtain the purified protein. This purified protein can then be used to identify compounds which bind to the receptor. Compounds thus identified can then be further evaluated using, for example, appropriate bioassays to confirm and/or characterize the pest control activity of the compound.

As an alternative to purifying TMOF receptors from their natural material, recombinant TMOF receptor protein can be expressed in an appropriate recombinant host that has been transformed with a polynucleotide sequence encoding the TMOF receptor. The polynucleotide sequence used to transform the appropriate host may comprise, for example, the polynucleotide coding sequence disclosed in SEQ ID NO. 43. The host may be transformed so as to express the TMOF receptor at the cell surface or, alternatively, the TMOF receptor may be retained intracellularly or secreted into the surrounding media. In any case, the expressed TMOF receptor may be isolated from the recombinant host using techniques known to those skilled in the art. The recombinant purified protein can then be used as described above to identify compounds which bind to the receptor. As an alternative embodiment, the receptor expressed at the surface of the recombinant cell can be used in conjunction with the whole cell to identify compounds which bind to the receptor.

In another embodiment, TMOF receptors of the subject invention can be applied to a chip or other suitable substrate to facilitate high throughput screening of potential pest control compounds.

Once compounds are identified which bind to the TMOF receptor, their pesticidal activity can be confirmed and/or characterized using bioassays known to those skilled in the art. The pesticide compounds of the subject invention can have activity against a variety of pests. These pests include agricultural pests which attack plants as well as pests of animals which attack humans, agricultural animals, domestic animals, and wild animals.

Preparation of novel pest control compounds. The novel pesticidal compounds of the invention can be prepared by well-known synthetic procedures. For example, the pesticidal polypeptides of the present invention can be prepared by the well-known Merrifield solid support method. See Merrifield (1963) *J. Amer. Chem. Soc.* 85:2149–2154 and Merrifield (1965) *Science* 150:178–185. This procedure, using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations, since removal of the excess reagents at each step is effected simply by washing the polymer.

Alternatively, these peptides can be prepared by use of well-known molecular biology procedures. Polynucleotide sequences encoding the pesticidal polypeptides of the invention can be readily synthesized. These polynucleotide sequences are a further aspect of the subject invention. These polynucleotides can be used to transform prokaryotic and eukaryotic cells, such as bacteria, insect, plant, or fungi cells for synthesis of the peptides of the invention. These polynucleotides may also be employed to modify viruses such as bacteriophages for use as cloning and/or expression vectors. One example of a cell line useful in accordance with the present invention includes, the insect cell line Sf9 (*Spodoptera rugiperda*), deposit number ATCC CRL 1711, which is available from the American Type Culture Collection, 12301 Parklawn Drive, Rockville, Md. 20852 USA. An example of a useful virus includes Baculovirus *Autographa Californica* Nuclear Polyhedrosis Virus AcNPV) which is available from Texas A&M University, Texas Agricultural Experiment Station, College Station, Tex. 77843, and has been described in Smith, G., and M. D. Summers 1978) *Virology* 89:517–527; and (1979) *J. Virology* 30:828–838. Other nuclear polyhedrosis viruses (See World Health Organization Technical Report No. 531) such as *Spodoptera frugiperda* (Sf MNPV), *Choristoneura fumiferana* (Cf MNPV) (Smith, G., and M. D. Summers [1981] *J. Virol.* 39:125–137), or *Spodoptera littoralis* (S1 NPV) (Harrap et al. [1977] *Virology* 79:14–31) can be used instead of *Autographa californica* NPV. Other insect cell lines can also be substituted for *Spodoptera frugiperda* (Sf9), for example, *Trichoplusia ni* (Volkman, L. E., and M. D. Summers [1975] *J. Virol.* 16:1630–1637), *Spodoptera exigua, Choristoneura fumiferana* (Smith, G., and M. D. Summers [1981] *J. Virol.* 39:125–137) and *Spodoptera littoralis* (Harrap, K. A. et al. [1977] *Virology* 79:14–31).

In yet another embodiment, the subject invention is directed to polynucleotides which encode the subject pest control peptides. Polynucleotides can be produced by routine methods known in the art. See S. L. Beaucage and M. H. Caruthers (1981), *Tetrahedran Lett.* 22:1859. The polynucleotides may usefully be presented as expression vectors or as expression cassettes for insertion into expression vectors.

If desired, the polynucleotides of the present invention can be amplified using PCR. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. et al. (1985) "Enzymatic Amplification of β-Globin Genomic Sequences and Restriction Site Analysis for Diagnosis of Sickle Cell Anemia," Science 230:1350–1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase results in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

PCR primers can be designed from the DNA sequences of the subject invention. In performing PCR amplification, a certain degree of mismatch can be tolerated between primer and template. Therefore, mutations, deletions and insertions (especially additions of nucleotides to the 5' end) of the exemplified sequences fall within the scope of the subject invention. These PCR primers can be used to amplify genes of interest from a sample. Thus, this is another method by which polynucleotide sequences encoding the subject peptides can be identified and characterized.

The various methods employed in the preparation of plasmids comprising the pesticidal polypeptide encoding polynucleotides of the present invention, and transformation of host organisms are well known in the art and are described, for example, in U.S. Pat. Nos. 5,011,909 and 5,130,253. These patents are incorporated herein by reference. These procedures are also described in Maniatis et al. (1982) *Molecular Cloning: A Laboratory Manual*, Cold Spring Harbor Laboratory, New York. Thus, it is within the skill of those in the genetic engineering art to extract DNA from microbial cells, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

Production of Recombinant Hosts. In another embodiment, the subject invention is directed to a prokaryotic or eukaryotic cell transformed with a polynucleotide encoding a polypeptide of Formula I or II. Hosts which may be employed according to techniques well known in the art for the production of the polypeptides of the present invention include unicellular microorganisms, such as prokaryotes, i.e., bacteria; and eukaryotes, such as fungi, including yeasts, algae, protozoa, molds, and the like, as well as plant cells, both in culture or in planta, and animal cells.

Furthermore, virsus may also be modified to comprise a polynucleotide encoding a pesticidal polypeptide according to the present invention. Specific bacteria which are susceptible to transformation include members of the Enterobacteriaceae, such as strains of *Escherichia coli*; Salmonella; Bacillaceae, such as *Bacillus subtilis*; Pseudomonas; Pneumococcus; Streptococcus; *Haemophilus influenzae*, and yeasts such as Saccharomyces, among others. In one embodiment of the present invention, the transformed host is *Bacillus sphaericus*, which is known to be highly specific for control of mosquito larvae. In a preferred embodiment, the host is *Bacillus sphaericus*, serotype H5a5b, available from Abbott Laboratories as VectoLex CG Biological Larvicide (EPA Reg. No. 275–77).

The polynucleotide sequences of the subject invention can be used to transform a host cell; for example, the polynucleotide sequences can be introduced directly into the genome of the transformable host cell or can first be incorporated into a vector which is then introduced into the host. Exemplary methods of incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

It is well known in the art that when synthesizing a gene for improved expression in a host cell it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable to limit this analysis to genes that are highly expressed by the host cell.

Thus, in one embodiment of the subject invention, prokaryotic or eukaryotic cells such as bacteria, algae, fungi, plant, or other cells can be genetically engineered, i.e., transformed with polynucleotides encoding the subject peptides to attain desired expression levels of the subject peptides. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for the host cell, and to eliminate sequences that cause destabilization, inappropriate polyadenylation, degradation and termination of RNA and to avoid sequences that constitute secondary structure hairpins and RNA splice sites. For example, in synthetic genes the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the polynucleotide sequences of this invention can be performed using standard technology known in the art. For example, a structural gene designed for enhanced expression in a host cell can be assembled within a DNA vector from chemically synthesized oligonucleotide duplex segments. Preferably the DNA vector or construct has a suitable origin of replication; a selectable marker, such as antibiotic resistance or fluorescence; appropriate termination sequences; and an operable promoter.

Furthermore, chimeric toxins may be used according to the subject invention. Methods have been developed for making useful chimeric toxins by combining portions of proteins. The individual polypeptides which are combined to form the pesticidal chimeras need not be pesticidal, so long as the combination of portions creates a chimeric protein which is pesticidal. The chimeric toxins may include portions from toxins which do not necessarily act upon the TMOF receptor, for example, toxins from *Bacillus thuringiensis* (*B.t.*). e.g., *B.t. israelensis, B.t. tenebrionis, B.t. san diego, B.t. aizawa, BHt. subtoxicus, B.t. alesti, B.t. gallaeriae, B.t. sotto, B.t. kurstaki, B.t. berliner, B.t. tolworthi, B.t. dendrolimus*, and *B.t. thuringiensis*, and delta endotoxins as described in U.S. Pat. No. 5,686,069.

With the teachings provided herein, one skilled in the art can readily produce and use the various toxins and polynucleotide sequences described herein.

The polynucleotide sequences and polypeptides useful according to the subject invention include not only the exemplified sequences but also fragments analogues, derivatives and variants thereof which retain some or all of the characteristic pesticidal activity of the TMOF peptides, or which exhibit improved activity as compared to the activity of the TMOF peptides. As used herein, the terms "variants" or "variations" of genes in reference to nucleotide sequences means nucleotide sequences encoding the same peptides or encoding equivalent peptides having pesticidal activity. As used herein, the term "equivalent peptides" refers to peptides having some or all of the same biological activity of the pesticidal peptides.

Variations of genes may be readily constructed using standard techniques for making point mutations. Also, fragments of these genes can be made using commercially available exonucleases or endonucleases according to standard procedures. For example, enzymes such as BAL31 or site-directed mutagenesis can be used to systematically excise nucleotides from the ends of these genes. Also, genes which encode active fragments may be obtained using a variety of restriction enzymes. Proteases may be used to directly obtain active fragments of these peptides.

Polynucleotide sequences encoding the pesticidal polypeptides of the present invention can be introduced into a wide variety of microbial or plant hosts. In the case of toxins, expression of the gene results, directly or indirectly, in the production and maintenance of the pesticide. With suitable microbial hosts, e.g., yeast or Chlorella, the microbes can be applied to the situs of the pest where they will proliferate and be ingested resulting in control of the pest. Alternatively, the microbe hosting the gene can be killed and optionally treated under conditions that retain and/or prolong the activity of the toxin and stabilize the cell. The treated cell, which retains the toxic activity, then can be applied to the environment of the target pest. In one embodiment, the host is transformed such that the gene encoding the pesticidal polypeptide is only expressed or maintained for a relatively short period of time, such as days or months, so that the material does not persist in the environment.

A wide variety of means are available for introducing a polynucleotide sequence encoding a pesticidal polypeptide into a host under conditions which allow for stable maintenance and expression of the gene. These methods are well known to those skilled in the art and are described, for example, in U.S. Pat. No. 5,135,867, which is incorporated herein by reference.

Synthetic genes that encode peptides that are functionally equivalent to the toxins of the subject invention can also be used to transform hosts. Methods for the production of synthetic genes can be found in, for example, U.S. Pat. No. 5,380,831.

Recombinant cells expressing a pest control compound can be treated to prolong the toxin activity and stabilize the cell. For example, the pesticidal polypeptides can be formulated as pesticide microcapsules comprising the pesticidal polypeptide within a cellular structure that has been stabilized and protects the pesticidal polypeptide when the microcapsule is applied to the environment of the target pest. Suitable host cells include either prokaryotes or eukaryotes. As hosts, of particular interest are the prokaryotes and the lower eukaryotes, such as algae and fungi. The cell is preferably intact and substantially in the proliferative form when treated, rather than in a spore form.

Treatment of the microbial cell, e.g., a microbe containing the polynucleotide sequence encoding the pesticidal polypeptide, can be by chemical or physical means, or by a combination of chemical and/or physical means, so long as the technique does not eliminate the pesticidal properties of the pesticidal polypeptide, nor eliminate the cellular capability of protecting the toxin. Methods for treatment of microbial cells are disclosed in U.S. Pat. Nos. 4,695,455 and 4,695,462.

Methods and Formulations for Control of Pests. Control of pests using the pest control compounds of the subject invention can be accomplished by a variety of methods known to those skilled in the art. These methods include, for example, the application of recombinant microbes to the pests (or their habitats, food sources, etc.), and the transformation of plants with genes (polynucleotide sequences) encoding the pesticidal polypeptides of the subject invention. Transformations can be accomplished by those skilled in the art using standard techniques. Materials necessary for these transformations are disclosed herein or are otherwise readily available to the skilled artisan.

The plant pests that can be controlled by the compounds of the subject invention include pests belonging to the orders Coleoptera, Lepidopterans, Hemiptera and Thysanoptera. These pests all belong to the phylum Arthropod. Other pests that can be controlled according to the subject invention include members of the orders Diptera, Siphonaptera, Hymenoptera and Phthiraptera. Other pests that can be controlled by the compounds of the subject invention include those in the family Arachnida, such as ticks, mites and spiders.

The use of the compounds of the subject invention to control pests can be accomplished readily by those skilled in the art having the benefit of the instant disclosure. For example, the compounds may be encapsulated, incorporated in a granular form, solubilized in water or other appropriate solvent, powdered, and included into any appropriate formulation for direct application to the pest or to a pest-inhabited locus. In a preferred embodiment for the control of plant pests, plants may be genetically transformed to express a pesticidal polypeptide, such that a pest feeding upon the plant will ingest pesticidal polypeptide and thereby be controlled.

Where the polynucleotide sequence is introduced via a suitable vector into a microbial host, and said host is applied to the environment in a living state, it is preferred that certain host microbes be used. In one aspect, preferred microbes are known to occupy the "phytosphere" (phylloplane, phyllosphere, rhizosphere, and/or rhizoplane) of one or more crops of interest or the situs where the pest proliferates. These microorganisms are selected so as to be capable of successfully competing in the particular environment (crop and other insect habitats) with the wild-type organisms, provide for stable maintenance and expression of the gene expressing the pesticidal polypeptide and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium, and algae, e.g., Chlorella. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. The pigmented microorganisms are preferred.

Formulated bait granules containing an attractant and the pesticidal polypeptides of the present invention, or recombinant microbes comprising toxin-encoding polynucleotide sequences, can be applied to a pest-inhabited locus, such as to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates or the like. The ingredients may include rheological agents, surfactants, emulsifiers, dispersants or polymers.

As would be appreciated by a person skilled in the art, the pesticidal concentration will vary widely depending upon the nature of the particular formulation, particularly whether it is a concentrate or to be used directly. The pesticide will be present in at least about 0.0001% by weight and may be 100% by weight. The dry formulations will have from about 0.0001–95% by weight of the pesticide while the liquid formulations will generally be from about 0.0001–60% by weight of the solids in the liquid phase. The formulations that contain cells will generally have from about 1 to about $10^{10}$ cells/mg. These formulations will be administered at about 50 mg (liquid or dry) to 1 kg or more per hectare.

The formulations can be applied to the environment of the pest, e.g., soil and foliage, by spraying, dusting, sprinkling or the like.

In applications to the environment of the target pest, the transformant strain can be applied to the natural habitat of the pest. In some cases,the transformant strain will grow in the pest upon ingestion, while continuing to produce the pesticidal polypiptide(s) The organism may be applied by a wide variety of methods known in the art, including pouring, spraying, soaking, injection into the soil, seed coating, seedling coating or spraying or the like.

In aquatic environments, pest control may be attained at or below the surface by adjusting the specific gravity of the microbe. This can be accomplished by, for example, varying the lipid content of the transformant microorganism strain. It is known that many indigenous aquatic algae float due to their lipid content. A variation in lipid content will allow the transformant strain to be distributed at desired depths below the water surface.

The pest control compounds may also be provided in tablets, pellets, briquettes, bricks, blocks and the like which are formulated to float, maintain a specified depth or sink as desired. In one embodiment the formulations, according to the present invention, are formulated to float on the surface of an aqueous medium; in another embodiment they are formulated to maintain a depth of 0 to 2 feet in an aqueous medium; in yet another embodiment the formulations are formulated to sink in an aqueous environment.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^5$ to $10^9$ cells/ml and may then be employed for introduction into the environment of the pest.

All of the U.S. patents and other references cited herein are hereby incorporated by reference, as are co-filed U.S. patent application Ser. No. 09/295,846, (UF-223) Transformed Cells Useful for the Control of Pests; U.S. patent application Ser. No. 09/295,849, (UF-216) Neuropeptides and their use for Pest Control; U.S. patent application Ser. No. 09/296,113, (UF-224) Materials and Methods Useful for the Control of Insect Larvae; and U.S. patent application Ser. No. 09/295,924, Compositions and Methods for Controlling Pests.

The following examples are simply illustrative of the practice of the present invention and should not be construed as limiting. All percentages are by weight and all solvent mixture proportions are by volume unless otherwise noted.

EXAMPLE 1

Effect of TMOF Analogs on Mosquito Larvae

TMOF can traverse the gut epithelium, enter the hemolymph and bind a gut receptor (Borovsky, D. and F.

Mahmood (1995) "Feeding the mosquito *Aedes aegypti* with TMOF and its analogs; effect on trypsin biosynthesis and egg development," *Regulatory Peptides* 57:273–281.; Borovsky et al. (1994) "Characterization and localization of mosquito-gut receptors for trypsin modulating oostatic factor using complementary peptide immunochemistry" *FASEB J*. 8:350–355.). This characteristic permits the testing of TMOF and its analogues by feeding them to mosquito and other pest larvae. To find out if truncated TMOF peptides have an effect on larval growth and development, a series of peptides were synthesized and tested by feeding them to mosquito larvae at concentrations of 0 to 5.0 mg/ml (Table 2). Individual, newly hatched *Aedes aegypti* larvae were maintained in separate microtiter plate wells on a diet of autoclaved yeast (1 mg/ml). The diet was supplemented with TMOF peptides (Table 2). An identical number of larvae maintained on yeast served as a control. Larvae fed on different concentrations of TMOF peptides (0 mg/ml to 5.0 mg/ml) were monitored for eight (8) days for survival and larval growth and development. All control groups survived and larval growth and development was normal. Since larvae swallow only a small portion of the yeast particles adsorbed the peptides, it is assumed that approximately 1 to 20 ng are taken orally at the high concentrations. The results are displayed in Table 2 as the Lethal Dose at 50% mortality (LD50;) of the TMOF peptides.

TABLE 2

The Effect of TMOF and its analogue peptides on mosquito larvae

| Compound | N | $LD_{50}$ mM ± S.E.M. | Compound | N | $LD_{50}$ Mm ± S.E.M. |
|---|---|---|---|---|---|
| 1. $YDPAP_6$ | 3 | 0.2 ± 0.02 | 23. DPA | 3 | 0.4 ± 0.03 |
| 2. $MPDYP_5$ | 3 | >3.0 | 24. (D)YDP | 3 | 0.51 ± 0.05 |
| 3. YDPAF | 3 | 0.33 ± 0.2 | 25. DAA | 3 | 0.91 ± 0.06 |
| 4. YEPAP | 3 | 0.35 ± 0.02 | 26. YDG | 3 | 0.95 ± 0.11 |
| 5. FDPAP | 3 | 0.37 ± 0.15 | 27. YDF | 3 | 0.97 ± 0.11 |
| 6. YDPLP | 3 | 1.5 ± 0.04 | 28. APA | 3 | 1.0 ± 0.07 |
| 7. YDPAL | 3 | 0.52 ± 0.03 | 29. AAP | 3 | 1.08 ± 0.07 |
| 8. YAPAP | 3 | 0.54 ± 0.13 | 30. YSF | 3 | 1.08 ± 0.12 |
| 9. YNPAP | 3 | 0.55 ± 0.03 | 31. DYP | 4 | 1.27 ± 0.17 |
| 10. (D)YDPAP | 3 | 0.56 ± 0.03 | 32. YDA | 3 | 1.6 ± 0.13 |
| 11. YFPAP | 3 | 0.64 ± 0.03 | 33. FDP | 3 | 1.98 ± 0.6 |
| 12. YDPAP | 3 | 1.64 ± 0.03 | 34. YDP | 5 | 2.3 ± 0.4 |
| 13. YDLAP | 3 | 0.6 ± 0.05 | 35. FSP | 3 | 2.3 ± 0.13 |
| 14. YDFAP | 3 | 0.74 ± 0.13 | 36. YAP | 3 | 2.3 ± 0.5 |
| 15. YDAAP | 3 | 1.0 ± 0.18 | 37. PAA | 3 | 2.4 ± 0.34 |
| 16. YDPGP | 5 | 1.1 ± 0.18 | 38. PAP | 3 | 3.17 ± 0.14 |
| 17. Y(D)DPAP | 3 | 1.2 ± 0.3 | 39. FAP | 3 | 3.8 ± 0.23 |
| 18. YSPAP | 3 | 1.4 ± 0.03 | 40. ADP | 3 | >6.6 |
| 19. YDPAA | 3 | 1.6 ± 0.13 | 41. YD | 3 | 1.24 ± 0.06 |

TABLE 2-continued

The Effect of TMOF and its analogue peptides on mosquito larvae

| Compound | N | $LD_{50}$ mM ± S.E.M. | Compound | N | $LD_{50}$ Mm ± S.E.M. |
|---|---|---|---|---|---|
| 20. YDPFP | 4 | 1.7 ± 0.4 | 42. DY | 3 | 3.0 ± 0.8 |
| 21. ADPAP | 4 | 2.0 ± 0.36 | | | |
| 22. Y(D)DP | 3 | 0.28 ± 0.01 | | | |

Groups of 12 to 24 mosquito larvae were incubated with different concentrations of TMOF and its analog peptides in 100 μl microtiter plates for 7 days. Results are expressed as $LD_{50}$ ± S.E.M.

EXAMPLE 2

Effect of TMOF Analogue Peptides on *Heliothis virescens*

Several analogues were chosen and were fed to fourth instar *Heliothis virescens* for seven (7) days and to first instars for fourteen (14) days (Tables 3 and 4). In both cases a reduction in weight gain and trypsin inhibition was noted (Tables 3 and 4).

Individual first instar and fourth instar larvae of *H. virescens* were maintained in separate plastic cups and were fed on artificial diet blocks on which different concentrations of TMOF (0 to 1.6 mg) were adsorbed. Larvae were fed for 5 to 14 days and larval weight and trypsin activity were measured at the end of the experimental periods. A reduction in larval weight and trypsin biosynthesis was observed in fourth instar larvae that were fed TMOF analogue peptides for 5 days (see Table 3 analogues 15, 14, and 18). When first instar larvae were fed for 14 days, an 18% and 26% reduction in weight was observed when analogues 15 and 14 were used (Table 4). These results indicate that the TMOF peptides of the subject invention control trypsin biosynthesis in *H. virescens* as was shown in mosquitoes and that these analogues can be used to control these agricultural pest insects.

These results indicate that short TMOF peptides can be used efficiently to block larval growth in mosquitos and other pests. An advantage of using short analogs is that they can penetrate the midgut much faster than longer peptides and are less expensive to synthesize by conventional chemical methods. Synthetic organic mimics of these peptides can also be prepared. These organic compounds can penetrate the larval skin and thus, can be used to spray plants for pest control.

TABLE 3

Effect of TMOF analogues on growth and trypsin biosynthesis on fourth instar *H. virescens*

| TMOF | Weight mg ± S.E.M. | | Weight | Trypsin | Inhibition |
|---|---|---|---|---|---|
| analog peptide | Start | End | Gain (mg) | μg ± S.E.M. | (% ± S.E.M.) |
| Control | 35.63 ± 1.54 | 219 ± 8.2 | 183.5 | 2.5 ± 0.15 | 0 |
| DYP(31) | 36.2 ± 2.4 | 216.7 ± 13 | 180.5 | 2.2 ± 0.3 | 14 ± 1.8 |
| YDPGP(16) | 31.7 ± 1.6 | 199.8 ± 11 | 163.1 | 2.1 ± 0.1 | 17 ± 1 |
| YDP(34) | 37 ± 1.5 | 223.4 ± 16 | 186.3 | 2.1 ± 0.3 | 19 ± 3.2 |
| ADPAP(21) | 35.7 ± 1.5 | 209.7 ± 12 | 174.1 | 2.4 ± 0.3 | 5 ± 0.6 |
| YDAAP(15) | 38.2 ± 1.3 | 217 ± 9.5 | 179 | 2.1 ± 0.2 | 17 ± 1.6 |
| YDFAP(14) | 37 ± 1.3 | 201 ± 12 | 164 | 2.1 ± 0.2 | 19 ± 1.5 |
| VSPAP(18) | 30.6 ± 1.2 | 188 ± 10.6 | 151 | 2.0 ± 0.2 | 19 ± 2 |

TABLE 3-continued

Effect of TMOF analogues on growth and trypsin biosynthesis on fourth instar *H. virescens*

| TMOF | Weight mg ± S.E.M. | | Weight | Trypsin | Inhibition |
|---|---|---|---|---|---|
| analog peptide | Start | End | Gain (mg) | μg ± S.E.M. | (% ± S.E.M.) |
| Y(D)DPAP(17) | 34.6 ± 2 | 188 ± 12 | 153 | 2.1 ± 0.2 | 15 ± 1.3 |

Fourth instar larvae were weighed and fed on synthetic food and 0.8 μg of TMOF analogs for 5 days. After feeding, larvae were weighed and guts were removed and groups of 3 to 4 guts were incubated with [$^3$H]DFP and analyzed for trypsin biosynthesis. Results are average of 3 to 10 experiments ± S.E.M.

TABLE 4

Feeding of *H. virescens* on TMOF analogs for 14 days

| TMOF analog | N | Number of Dead Larvae | Weight (mg) ± S.E.M. | Weight Reduction (%) ± S.E.M. |
|---|---|---|---|---|
| Control | 8 | 2 | 163 ± 12 | 0 |
| DYP(31) | 9 | 1 | 149 ± 9 | 9 ± 0.5 |
| YDPGP(16) | 8 | 2 | 153 ± 10 | 6 ± 0.4 |
| YDP(34) | 9 | 0 | 157 ± 10 | 4 ± 0.2 |
| ADPAD(21) | 10 | 0 | 141 ± 9 | 7 ± 0.4 |
| YDAAP(15) | 10 | 0 | 133 ± 7 | 18 ± 1 |
| YDFAP(14) | 9 | 1 | 121 ± 7 | 26 ± 1.5 |
| YSPAD(18) | 10 | 0 | 168 ± 11 | 0 |
| Y(D)DPAP(17) | 9 | 1 | 152 ± 27 | 7 ± 1 |

First instar larvae were fed individually 1.6 μg of TMOF analogs for 14 days. After feeding, the weight of each larvae was determined and expressed as an average of 9 to 10 determinations ± S.E.M.

EXAMPLE 3

Biological Activity of Compounds Which Bind to TMOF Receptors

Control agents which bind with TMOF receptors can be tested to confirm and characterize pest control activity. Many bioassays are known to those skilled in the art for the purpose of evaluating pesticidal activity. Assays for evaluating mosquito control activity are known to those skilled in the art and are described in, for example, U.S. Pat. No. 5,436,002. Bioassays for evaluating the pest control activity against other targets are also known to those skilled in the art and are described in, for example, U.S. Pat. Nos. 5,596,071; 5,188,960; and 5,366,892.

EXAMPLE 4

Bioassays for Activity Against Lepidopterons and Coleopterans

Biological activity of the pesticidal compounds of the subject invention can be confirmed using standard bioassay procedures. One such assay is the budworm-bollworm (*Heliothis virescens* [Fabricius] and *Helicoverpa zea* [Boddie]) assay. Lepidoptera bioassays can be conducted with either surface application to artificial insect diet or diet incorporation of samples. All Lepidopteran insects can be tested from the neonate stage to the final instar. All assays can be conducted with artificial diet, such as toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no pesticidal polypeptide(s) serve as the control. First instar larvae (USDA-ARS, Stoneville, Miss.) can be placed onto the diet mixture. Wells can then be sealed with Mylar sheeting (ClearLam Packaging, Ill.) using a tacking iron, and several pinholes can be made in each well to provide gas exchange. Larvae can be maintained at 25° C. for 6 days in a 14:10 (light:dark)holding room. Mortality and stunting can be recorded after six days.

Bioassay by the top load method can utilize the same sample and diet preparations as listed above. The samples can be applied to the surface of the insect diet. In a specific embodiment, surface area can range from 0.3 to approximately 0.8 $cm^2$ depending on the tray size; 96 well tissue culture plates can be used in addition to the format described above. Following application, samples can be allowed to air dry before insect infestation. A water blank containing no pesticidal polypeptide(s) serve as the control. Eggs can be applied to each treated well and then can be sealed with Mylar sheeting (ClearLam Packaging, Ill.) using a tacking iron, and pinholes can be made in each well to provide gas exchange. Bioassays can be maintained at 25° C. for 7 days in a 14:10 (light:dark) or 28° C. for 4 days in a 14:10 (light:dark) holding room. Mortality and insect stunting can be recorded at the end of each bioassay.

Another assay useful according to the subject invention is the Western Corn Rootworm assay. Compounds can be bioassayed for pesticidal activity against neonate Western Corn Rootworm larvae (*Diabrotica virgifera virgifera*) via top-loading of sample onto an agar-based artificial diet. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays can be maintained held in darkness at 25° C., and mortality scored after four days.

Analogous bioassays can be performed by those skilled in the art to assess activity against other pests, such as the black cutworm (*Agrotis ipsilon*).

EXAMPLE 5

Target Pests

Pesticidal compounds of the subject invention can be used, alone or in combination with other pesticides, to control one or more non-mammalian pests. These pests may be, for example, those listed in Table 5. Activity can readily be confirmed using the bioassays provided herein, adaptations of these bioassays, and/or other bioassays well known to those skilled in the art.

TABLE 5

Examples of Target pest species

| ORDER/Common Name | Latin Name |
|---|---|
| LEPIDOPTERA | |
| European Corn Borer | *Ostrinia nubilalis* |
| European Corn Borer resistant to Cry1A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Cabbage Looper | *Trichopluia nil* |
| Spilosoma | *Spilosoma virginica* |
| Bertha Armyworm | *Mamestra configurata* |
| Diamondback Moth | *Plutella xylostells* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 6

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for transforming higher plants, e,g., pBR322, pUC series, M13mp series, pACYC184, etc. Accordingly, the sequence encoding the pesticidal peptide can be inserted into the vector at a suitable restriction site. The resulting plasmid can be used for transformation into *E. coli*. The *E. coli* cells can be cultivated in a suitable nutrient medium, then harvested and lysed. The plasmid can be recovered. Sequence analysis, restriction analysis, electrophoresis, and other biochemical and/or molecular biological methods can be generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti plasmid (the tumor-inducing plasmid of the plant-pathogenic bacterium *Agrobacterium tumefaciens*) or Ri plasmid (the root-inducing plasmid of *Agrobacterium rhizogenes*) can be used for the transformation of the plant cell, then at least the right border, but often the right and the left border of the Ti or Ri plasmid T-DNA ("Transferred DNA"), must be joined as the flanking region of the genes to be inserted.

A large number of techniques are available for inserting DNA into a plant host cell. These techniques include transformation with T-DNA using *Agrobacterium tumefaciens* or *Agrobacterium rhizogenes* as transformation agent, fusion, injection, biolistics (microparticle bombardment), or electroporation as well as other possible methods.

One of the most widely used approaches for the introduction of DNA into plant cells exploits the natural DNA-transferring properties of *Agrobacterium tumefaciens* and *Agrobacterium rhizogenes*, the two species which cause crown gall and hairy root. Their ability to cause disease depends on the presence of large plasmids, in excess of 100 kb, which are referred to as the Ti and Ri plasmids, respectively.

A region referred to as the T-DNA ("Transferred DNA") is transferred from an infecting Agrobacterium cell into the nucleus of the plant cell, where it is integrated into the plant genome. Transfer of the T-DNA depends on a set of genes called vir if they are on the Ti plasmid, or chv if they are on the chromosome. These genes are induced in response to various compounds in exudates from wounded plants. The T-DNA itself is flanked by repeated sequences of around 25 base pairs, called border repeats (or left and right borders). The T-DNA contains a group of genes referred to as the onc genes, which are responsible for the oncogenicity of the T-DNA.

The use of Agrobacterium in the genetic manipulation of plants involves the insertion of foreign DNA into the T-DNA of a bacterial cell and subsequent transfer of the DNA by the transformed bacterium into the plant. As long as the necessary proteins are provided by the bacterium, any sequences flanked by the T-DNA border repeats can be transferred into the recipient plant cell genome. The Ti plasmids are too large to manipulate directly, but this problem can be circumvented by using cointegrative and binary systems.

The two main components of a cointegrative system are a Ti plasmid that has typically been modified by the replacement of material between the border repeats (including the onc sequences) by pBR322; and an intermediate vector, which is a modified pBR322 containing an extra marker, such as kanamycin resistance. The gene to be introduced into the target plant is first cloned into the intermediate vector, and this construct is then introduced into Agrobacterium containing the Ti vector. The pBR322-based plasmid cannot replicate efficiently inside Agrobacterium, so selection for kanamycin resistance identifies those Agrobacterium cells where the pBR322-based intermediate plasmid has been integrated by homologous recombination into the Ti plasmid. Because the recombination is homologous, it will take place across the pBR322 sequences and therefore result in integration between the border repeats.

The need for cointegration of the plasmids can be circumvented by use of a binary vector, such as pBin19, a small plasmid containing a pair of left and right borders. The lacZ region, located within the borders, facilitates insertion and detection of DNA. A neomycin phosphotransferase gene, typically modified for expression in plants by addition of nopaline synthase expression sequences, is also present within the borders. Outside the left and right borders, there is typically a kanamycin resistance gene that will function in prokaryotes and a broad host-range origin derived from the plasmid pRK252. The proteins that catalyze transfer of the T-DNA into the host plant do not have to be cis-encoded (i. e., do not have to be encoded by the same molecule). Therefore, if the binary vector is introduced into Agrobacterium that already contains a resident Ti plasmid, the resident plasmid can provide all the functions needed to transfer into a plant nucleus the DNA between the borders of the binary vector. Other, more sophisticated binary vectors, are also known in the art, for example pROK1. These vectors typically have plant promoters incorporated to drive expression. Others have cos sites to allow packaging into lambda phage heads.

When the correct sequences have been incorporated into a vector (whether binary or cointegrative), the vector must then be transferred to an Agrobacterium strain carrying an appropriate Ti plasmid. This is usually accomplished either by electroporation with naked DNA or by a triparental mating involving the Agrobacterium strain, an *E. coli* strain containing the vector to be transferred, and an *E. coli* strain with a plasmid capable of mobilizing the binary or intermediate vector into Agrobacterium.

Once the binary vector of the cointegrative vector has been introduced into a suitable Agrobacterium strain (and cointegration has occurred), the next stage is to permit the Agrobacterium to infect plant cells. Various methods exist, including inoculation of intact plants with Agrobacterium cultures by injection, but the most widely used is to incubate discs cut from leaves of the target plant with an Agrobacterium culture. The bacterium will attack cells around the edge of the wounded leaf disc and transfer its T-DNA back into them. The leaf discs are then transferred to a suitable medium to select for transformation. The neomycin phosphotransferase gene is widely used, conferring resistance to aminoglycoside antibiotics, such as neomycin, kanamycin, and G518. On a suitable selective medium, shoots form around the edges of the treated leaf discs. The shoots can then be regenerated into intact plants. See Howe, *Gene Cloning and Manipulation* (1995).

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a pesticidal polypeptide will be used. The pesticidal polypeptide typically will encode less than about 50% of the full length toxin but may be longer or shorter than TMOF.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A pesticidal peptide consisting of an amino acid sequence selected from the group consisting of: SEQ ID NO. 17, SEQ ID NO. 19, SEQ ID NO. 21, SEQ ID NO. 22, SEQ ID NO. 23, SEQ ID NO. 24, SEQ ID NO. 25, SEQ ID NO. 26, SEQ ID NO. 27 SEQ ID NO. 28, SEQ ID NO. 30, SEQ ID NO. 32, SEQ ID NO. 33, SEQ ID NO. 34, SEQ ID NO. 35, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, and SEQ ID NO. 56.

2. The pesticidal peptide of claim 1 consisting of the amino acid sequence set forth in SEQ ID NO. 17.

3. The pesticidal peptide of claim 1 consisting of the amino acid sequence set forth in SEQ ID NO. 19.

4. The pesticidal peptide of claim 1 consisting of the amino acid sequence set forth in SEQ ID NO. 21.

5. The pesticidal peptide of claim 1 consisting of the amino acid sequence set forth in SEQ ID NO. 22.

6. The pesticidal peptide of claim 1 consisting of the amino acid sequence set forth in SEQ ID NO. 23.

7. The pesticidal peptide of claim 1 consisting of the amino acid sequence set forth in SEQ ID NO. 24.

8. The pesticidal peptide of claim 1 consisting of the amino acid sequence set forth in SEQ ID NO. 25.

9. The pesticidal peptide of claim 1 consisting of the amino acid sequence set forth in SEQ ID NO. 26.

10. The pesticidal peptide of claim 1 consisting of the amino acid sequence set forth in SEQ ID NO. 27.

11. The pesticidal peptide of claim 1 consisting of the amino acid sequence set forth in SEQ ID NO. 28.

12. The pesticidal peptide of claim 1 consisting of the amino acid sequence set forth in SEQ ID NO. 30.

13. The pesticidal peptide of claim 1 consisting of the amino acid sequence set forth in SEQ ID NO. 32.

14. The pesticidal peptide of claim 1 consisting of the amino acid sequence set forth in SEQ ED NO. 33.

15. The pesticidal peptide of claim 1 consisting of the amino acid sequence set forth in SEQ ID NO. 34.

16. The pesticidal peptide of claim 1 consisting of the amino acid sequence set forth in SEQ ID NO. 35.

17. The pesticidal peptide of claim 1 consisting of the amino acid sequence set forth in SEQ ID NO. 37.

18. The pesticidal peptide of claim 1 consisting of the amino acid sequence set forth in SEQ ID NO. 38.

19. The pesticidal peptide of claim 1 consisting of the amino acid sequence set forth in SEQ ID NO. 39.

20. The pesticidal peptide of claim 1 consisting of the amino acid sequence set forth in SEQ ID NO. 40.

21. The pesticidal peptide of claim 1 consisting of the amino acid sequence set forth in SEQ ID NO. 41.

22. The pesticidal peptide of claim 1 consisting of the amino acid sequence set forth in SEQ ID NO. 42.

23. The pesticidal peptide of claim 1 consisting of the amino acid sequence set forth in SEQ ID NO. 43.

24. The pesticidal peptide of claim 1 consisting of the amino acid sequence set forth in SEQ ID NO. 44.

25. The pesticidal peptide of claim 1 consisting of the amino acid sequence set forth in SEQ ID NO. 45.

26. The pesticidal peptide of claim 1 consisting of the amino acid sequence set forth in SEQ ID NO. 47.

27. The pesticidal peptide of claim 1 consisting of the amino acid sequence set forth in SEQ ID NO. 48.

28. The pesticidal peptide of claim 1 consisting of the amino acid sequence set forth in SEQ ID NO. 49.

29. The pesticidal peptide of claim 1 consisting of the amino acid sequence set forth in SEQ ID NO. 50.

30. The pesticidal peptide of claim 1 consisting of the amino acid sequence set forth in SEQ ID NO. 51.

31. The pesticidal peptide of claim 1 consisting of the amino acid sequence set forth in SEQ ID NO. 52.

32. The pesticidal peptide of claim 1 consisting of the amino acid sequence set forth in SEQ ID NO. 53.

33. The pesticidal peptide of claim 1 consisting of the amino acid sequence set forth in SEQ ID NO 54.

34. The pesticidal peptide of claim 1 consisting of the amino acid sequence set forth in SEQ ID NO. 55.

35. The pesticidal peptide of claim 1 consisting of the amino acid sequence set forth in SEQ ID NO. 56.

36. A fusion peptide comprising a pesticidal peptide joined to a heterologous peptide, wherein said pesticidal peptide consists of an amino acid sequence selected from the group consisting of: SEQ ID NO, 17, SEQ ID NO 19, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 34, SEQ ID NO. 35, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56.

37. The fusion peptide, according to claim 36, wherein said pesticidal peptide is currently attached to said heterologous peptide.

* * * * *

UNITED STATES PATENT AND TRADEMARK OFFICE
CERTIFICATE OF CORRECTION

PATENT NO. : 6,413,530 B1 
DATED : July 2, 2002
INVENTOR(S) : Dov Borovsky and Russell J. Linderman It is certified that error appears in the above-identified patent and that said Letters Patent is hereby corrected as shown below:

Column 1,
Line 25, "*Trypanasomacruzi*" should read -- *Trypanasoma cruzi* --.

Columnn 2,
Line 56, "reparation" should read -- preparation --.

Column 3,
Line 2, "[1990]*FASEB J.*" should read -- [1990] *FASEB J.* --.
Line 6, "YDPAP, YDPAPP, YDPAPPP, and YDPAPPPP." should read -- YDPAP (SEQ ID NO. 11), YDPAPP (SEQ ID NO. 12), YDPAPPP (SEQ ID NO. 13), and YDPAPPPP (SEQ ID NO. 14). --.
Line 53, "amid" should read -- amide --.
Line 54, "Ala-Pro-Ser-Arg-Leu-Arg-Phe-amide" should read -- Ala-Pro-Ser-Leu-Arg-Leu-Arg-Phe-amide --.

Column 4,
Line 7, "$A^1A^2A^3A^4A^5F$ (Formula I)" should read -- $A^1A^2A^3A^4A^5Fl$ (Formula I) (SEQ ID No. 5) --.
Line 9, "consisting of Y, A," should read -- consisting of A, --.
Line 20, "F is a" should read -- Fl is a --.
Lines 21-22, "P, PP, PPP, PPPP, and PPPPP." should read -- P, PP, PPP, PPPP (SEQ ID NO. 6), and PPPPP (SEQ ID NO. 7). --.
Lines 24-25, "$YDPAP_6$, $DYPAP_6$, $PAP_6$, YDPAP, $YDPAP_2$, $YDPAP_3$, $YDPAP_4$, NPTNLH, or DF-OMe." should read -- $YDPAP_6$, (SEQ ID NO. 8), $DYPAP_6$ (SEQ ID NO. 9), $PAP_6$ (SEQ ID NO. 10), YDPAP (SEQ ID NO. 11), $YDPAP_2$ (SEQ ID NO. 12), $YDPAP_3$ (SEQ ID NO. 13), $YDPAP_4$ (SEQ ID NO. 14), NPTNLH (SEQ ID NO. 15), or DF-OMe. --.
Line 31, "Instill" should read -- In still --.
Line 32, "Formula I," should read -- Formula I (SEQ ID NO. 5). --.
Lines 33-34, "F of Formula I are present and F is" should read -- Fl of Formula I are present and Fl is --.
Lines 36-37, "F of Formula I are present and F is" should read -- Fl of Formula I are present and Fl is --.
Line 39, "F of Formula I are present and F is" should read -- Fl of Formula I are present and Fl is --.
Line 46, "(Formula II)," should read -- (Formula II) (SEQ ID NO. 16), --.

UNITED STATES PATENT AND TRADEMARK OFFICE

CERTIFICATE OF CORRECTION

PATENT NO. : 6,413,530 B1 
DATED : July 2, 2002
INVENTOR(S) : Dov Borovsky and Russell J. Linderman It is certified that error appears in the above-identified patent and that said Letters Patent is hereby corrected as shown below:

Column 6,
Lines 53-57, "SEQ ID NO. 1 is the amino acid sequence for TMOF.
SEQ ID NOS. 2-42 are TMOF peptide analogs according to thee subject invention.
SEQ ID NOS. 43-44 are TMOF receptors according to the subject invention." should read
-- SEQ ID NO. 1 is a neuropeptide designated NPF I.
SEQ ID NO. 2 is a neuropeptide designated NPF II.
SEQ ID NO. 3 is a polynucleotide encoding an amino acid sequence of a TMOF receptor.
SEQ ID NO. 4 is an amino acid sequence of a TMOF receptor.
SEQ ID NO. 5-60 are pesticidal peptides of the subject invention. --.

Column 7,
Line 4, $A^1A^2A^3A^4A^5F$ (Formula I)" should read -- $A^1A^2A^3A^4A^5Fl$ (Formula I) (SEQ ID NO. 5) --.
Line 7, "consisting of Y, A," should read -- consisting of A, --.
Line 18, "F is a" should read -- Fl is a --.
Lines 19-20, "P, PP, PPP, PPPP, and PPPPP." should read -- P, PP, PPP, PPPP (SEQ ID NO. 6), and PPPPP (SEQ ID NO. 7). --.
Lines 21-23, "$YDPAP_6$, $DYPAP_6$, $PAP_6$, YDPAP, $YDPAP_2$, $YDPAP_3$, $YDPAP_4$, NPTNLH, or DF-OMe." should read -- $YDPAP_6$ (SEQ ID NO. 8), $DYPAP_6$ (SEQ ID NO. 9), $PAP_6$ (SEQ ID NO. 10), YDPAP (SEQ ID NO. 11), $YDPAP_2$ (SEQ ID NO. 12), $YDPAP_3$ (SEQ ID NO. 13), $YDPAP_4$ (SEQ ID NO. 14), NPTNLH (SEQ ID NO. 15), or DF-OMe. --.
Lines 26 and 30, "Formula I." should read -- Formula I (SEQ ID NO. 5). --.
Lines 31-32 and 34-35, "F of formula I are present and F is" should read -- Fl of Formula I are present and Fl is --.
Line 37, "F of Formula I are present,. and F is" should read -- Fl of Formula I are present and Fl is --.
Line 43, "(Formula II)" should read -- (Formula II) (SEQ ID NO. 16) --.
Line 64, "2.0 pmole/ml" should read -- 2.0 μmole/ml --.

Column 8,
Lines 37-38, "Formulas I and/or II" should read -- Formulas I and/or II (SEQ ID Nos. 5 and 16) --.
Line 60, "omithine" should read -- ornithine --.

UNITED STATES PATENT AND TRADEMARK OFFICE
CERTIFICATE OF CORRECTION

PATENT NO. : 6,413,530 B1 
DATED : July 2, 2002
INVENTOR(S) : Dov Borovsky and Russell J. Linderman It is certified that error appears in the above-identified patent and that said Letters Patent is hereby corrected as shown below:

Column 9,
Line 5, "Formulas I and/or II," should read-- Formulas I and/or II (SEQ ID Nos. 5 and 16), --.
Lines 29 and 38, "SEQ ID NO. 44." should read -- SEQ ID NO. 4. --.
Line 36, "SEQ ID NO. 43" should read -- SEQ ID NO. 3 --.

Column 12,
Lines 1-2, "SEQ ID NO. 43." should read -- SEQ ID NO. 3. --.
Line 53, "*rugiperda*" should read -- *frugiperda* --.
Line 61, "1978)" should read -- (1978) --.

Column 15,
Line 28, "*BHt. subtoxicus*" should read -- *B.t. subtoxicus* --.

Column 19,
Line 25, "(LD50" should read -- $LD_{50}$ --.

Column 19, Table 2,
Lines 2-3,
"Compound N $LD_{50}$ mM ± S.E.M. Compound N $LD_{50}$ Mm ± S.E.M."
should read
--Compound SEQ ID NO. N $LD_{50}$ mM ± S.E.M. Compound SEQ ID NO. N $LD_{50}$ Mm ± S.E.M.--.

Columns 19-20, Table 2,

Compound 1, "YDPAP$_6$ 3 0.2 ± 0.02" should read
--YDPAP$_6$ 8 3 0.2 ± 0.02--.

Compound 2, "MPDYP$_5$ 3 >3.0" should read
--MPDYP$_5$ 29 3 >3.0--.

Compound 3, "YDPAF 3 0.33 ± 0.2" should read
--YDPAF 44 3 0.33 ± 0.2--.

UNITED STATES PATENT AND TRADEMARK OFFICE
CERTIFICATE OF CORRECTION

PATENT NO. : 6,413,530 B1
DATED : July 2, 2002
INVENTOR(S) : Dov Borovsky and Russell J. Linderman It is certified that error appears in the above-identified patent and that said Letters Patent is hereby corrected as shown below:

Columns 19-20, Table 2, cont'd,

Compound 4, "YEPAP 3 0.35 ± 0.02" should read
--YEPAP 50 3 0.35 ± 0.02--.

Compound 5, "FDPAP 3 0.37 ± 0.15" should read
--FDPAP 27 3 0.37 ± 0.15--.

Compound 6, "YDPLP 3 1.5 ± 0.04" should read
--YDPLP 49 3 1.5 ± 0.04--.

Compound 7, "YDPAL 3 0.52 ± 0.03" should read
--YDPAL 45 3 0.52 ± 0.03--.

Compound 8, "YAPAP 3 0.54 ± 0.13" should read
--YAPAP 54 3 0.54 ± 0.13--.

Compound 9, "YNPAP 3 0.55 ± 0.03" should read
-- YNPAP 52 3 0.55 ± 0.03 --.

Compound 10, "(D)YDPAP 3 0.56 ± 0.03" should read
-- (D)YDPAP 46 3 0.56 ± 0.03 --.

Compound 11, "YFPAP 3 0.64 ± 0.03" should read
-- YFPAP 51 3 0.64 ± 0.03 --.

Compound 12, "YDPAP 3 1.64 ± 0.03" should read
-- YDPAP 11 3 1.64 ± 0.03 --.

Compound 13, "YDLAP 3 0.6 ± 0.05" should read
-- YDLAP 41 3 0.6 ± 0.05 --.

UNITED STATES PATENT AND TRADEMARK OFFICE
CERTIFICATE OF CORRECTION

PATENT NO. : 6,413,530 B1
DATED : July 2, 2002

INVENTOR(S) : Dov Borovsky and Russell J. Linderman

It is certified that error appears in the above-identified patent and that said Letters Patent is hereby corrected as shown below:

Column 20, Table 2,

Lines 2-3,
"Compound N $LD_{50}$ mM ± S.E.M. Compound N $LD_{50}$ Mm ± S.E.M."
should read
--Compound SEQ ID NO. N $LD_{50}$ mM ± S.E.M. Compound SEQ ID NO. N $LD_{50}$ Mm ± S.E.M.--.

Columns 19-20, Table 2,
Compound 14, "YDFAP 3 0.74 ± 0.13" should read
-- YDFAP 39 3 0.74 ± 0.13 --.

Compound 15, "YDAAP 3 1.0 ± 0.18" should read
-- YDAAP 37 3 1.0 ± 0.18 --.

Compound 16, "YDPGP 5 1.1 ± 0.18" should read
-- YDPGP 48 5 1.1 ± 0.18 --.

Compound 17, "Y(D)DPAP 3 1.2 ± 0.3" should read
-- Y(D)DPAP 33 3 1.2 ± 0.3 --.

Compound 18, "YSPAP 3 1.4 ± 0.03" should read
-- YSPAP 55 3 1.4 ± 0.03 --.

Compound 19, "YDPAA 3 1.6 ± 0.13" should read
-- YDPAA 56 3 1.6 ± 0.13 --.

Compound 20, "YDPFP 4 1.7 ± 0.4" should read
-- YDPFP 47 4 1.7 ± 0.4 --.

Compound 21, "ADPAP 4 2.0 ± 0.36" should read
-- ADPAP 19 4 2.0 ± 0.36 --.

Compound 22, "Y(D)DP 3 0.28 ± 0.01" should read
-- Y(D)DP 32 3 0.28 ± 0.01 --.

Compound 23, "DPA 3 0.4 ± 0.03" should read
-- DPA 22 3 0.4 ± 0.03 --.

UNITED STATES PATENT AND TRADEMARK OFFICE

CERTIFICATE OF CORRECTION

PATENT NO. : 6,413,530 B1 
DATED : July 2, 2002
INVENTOR(S) : Dov Borovsky and Russell J. Linderman It is certified that error appears in the above-identified patent and that said Letters Patent is hereby corrected as shown below:

Columns 19-20, Table 2 cont'd,
Compound 24, "(D)YDP 3 0.51 ± 0.05" should read
-- (D)YDP 43 3 0.51 ± 0.05 --.

Compound 25, "DAA 3 0.91 ± 0.06" should read
-- DAA 21 4 0.91 ± 0.06 --.

Compound 26, "YDG 3 0.95 ± 0.11" should read
-- YDG 40 4 0.95 ± 0.11 --.

Compound 27, "YDF 3 0.97 ± 0.11" should read
-- YDF 38 3 0.97 ± 0.11 --.

Compound 28, "APA 3 1.0 ± 0.07" should read
-- APA 20 3 1.0 ± 0.07 --.

Compound 29, "AAP 3 1.08 ± 0.07" should read
-- AAP 17 3 1.08 ± 0.07 --.

Compound 30, "YSF 3 1.08 ± 0.12" should read
-- YSF 53 3 1.08 ± 0.12 --.

Compound 31, "DYP 4 1.27 ± 0.17" should read
-- DYP 24 4 1.27 ± 0.17 --.

Compound 32, "YDA 3 1.6 ± 0.13" should read
-- YDA 36 3 1.6 ± 0.13 --.

Compound 33, "FDP 3 1.98 ± 0.6" should read
-- FDP 26 3 1.98± 0.6 --.

Compound 34, "YDP 5 2.3 ± 0.4" should read -- YDP 42 5 2.3 ± 0.4 --.
Compound 35, "FSP 3 2.3 ± 0.13" should read -- FSP 28 3 2.3 ± 0.13 --.
Compound 36, "YAP 3 2.3 ± 0.5" should read -- YAP 34 3 2.3 ± 0.5 --.
Compound 37, "PAA 3 2.4 ± 0.34" should read -- PAA 30 3 2.4 ± 0.34 --.
Compound 38, "PAP 3 3.17 ± 0.14" should read -- PAP 31 3 3.17 ± 0.14 --.
Compound 39, "FAP 3 3.8 ± 0.23" should read -- FAP 25 3 3.8 ± 0.23 --.
Compound 40, "ADP 3 >6.6" should read -- ADP 18 3 >6.6 --.
Compound 41, "YD 3 1.24 ± 0.06" should read -- YD 35 3 1.24 ± 0.06 --.

UNITED STATES PATENT AND TRADEMARK OFFICE
CERTIFICATE OF CORRECTION

PATENT NO. : 6,413,530 B1 
DATED : July 2, 2002
INVENTOR(S) : Dov Borovsky and Russell J. Linderman It is certified that error appears in the above-identified patent and that said Letters Patent is hereby corrected as shown below:

Columns 19-20, Table 2, cont'd,
Compound 42, "DY 3 3.0 ± 0.8" should read -- DY 23 3 3.0 ± 0.8 --.

Column 20, Table 3,
Lines 3-5, "TMOF Weight
mg ± S.E.M.
analog peptide start end"
should read
--TMOF SEQ Weight
analog peptide ID NO. mg ± S.E.M.
start end --.

Column 21, Table 3,
Lines 3-5, "TMOF Weight
mg ± S.E.M.
analog peptide start end"
should read
-- TMOF SEQ Weight
analog peptide ID NO. mg ± S.E.M.
start end --.

Columns 20-21, Table 3,
Line 7, "DYP(31) 36.2 ± 2.4 216.7 ± 13" should read
-- DYP(31) 24 36.2 ± 2.4 216.7 ± 13 --.
Line 8, "YDPGP(16) 31.7 ± 1.6 199.8 + 11" should read
-- YDPGP(16) 48 31.7 ± 1.6 199.8 ± 11 --.

UNITED STATES PATENT AND TRADEMARK OFFICE
CERTIFICATE OF CORRECTION

PATENT NO. : 6,413,530 B1 
DATED : July 2, 2002
INVENTOR(S) : Dov Borovsky and Russell J. Linderman It is certified that error appears in the above-identified patent and that said Letters Patent is hereby corrected as shown below:

Columns 20-21, Table 3, cont'd,
Line 9, "YDP(34) 37 ± 1.5 223.4 ± 16" should read
-- YDP(34) 42 37 ± 1.5 223.4 ± 16 --.

Line 10, "ADPAP(21) 35.7 ± 1.5 209.7 ± 12" should read
-- ADPAP(21) 19 35.7 ± 1.5 209.7 ± 12 --.

Line 11, "YDAAP(15) 38.2 ± 1.3 217 ± 9.5" should read
-- YDAAP(15) 37 38.2 ± 1.3 217 ± 9.5 --.

Line 12, "YDFAP(14) 37 ± 1.3 201 ± 12" should read
-- YDFAP(14) 39 37 ± 1.3 201 ± 12 --.

Line 13, "VSPAP(18) 30.6 ± 1.2 1.88 ± 10.6" should read
-- YSPAP(18) 55 30.6 ± 1.2 188 ± 10.6 --.

Line 14, "Y(D)DPAP(17) 34.6 ± 2 188 ± 12" should read
-- Y(D)DPAP(17) 33 34.6 + 2 188 ± 12 --.

Column 21, Table 4,
Lines 3-4, "TMOF analog N Number of Dead Larvae"
should read
-- TMOF analog SEQ ID NO. N Number of Dead Larvae --.
Line 6, "DYP(31) 9 1" should read -- DYP(31) 24 9 1 --.
Line 7, "YDPGP(16) 8 2" should read -- YDPGP(16) 48 8 2 --.
Line 8, "YDP(34) 9 0" should read -- YDP(34) 42 9 0 --.
Line 9, "ADPAD(21) 10 0" should read -- ADPAP(21) 19 10 0 --.
Line 10, "YDAAP(15) 10 0" should read -- YDAAP(15) 37 10 0 --.
Line 11, "YDFAP(14) 9 1" should read -- YDFAP(14) 39 9 1 --.
Line 12, "YSPAD(18) 10 0" should read -- YSPAP(18) 55 10 0 --.
Line 13,"Y(D)DPAP(17) 9 1" should read -- Y(D)DPAP(17) 33 9 1 --.

Column 23,
Line 22, "*Trichopluia nil*" should read -- *Trichopluia niI* --.

Column 49,
Line 55, "SEQ ED NO. 33." should read -- SEQ ID NO. 33. --.

UNITED STATES PATENT AND TRADEMARK OFFICE
CERTIFICATE OF CORRECTION

PATENT NO. : 6,413,530 B1
DATED : July 2, 2002
INVENTOR(S) : Dov Borovsky and Russell J. Linderman It is certified that error appears in the above-identified patent and that said Letters Patent is hereby corrected as shown below:

Column 50,
Line 52, “SEQ ID NO, 17, SEQ ID NO 19,” should read -- SEQ ID NO. 17, SEQ ID NO. 19, --.
Line 64, “currently” should read -- covalently --.

Signed and Sealed this

Twentieth Day of May, 2003

JAMES E. ROGAN
*Director of the United States Patent and Trademark Office*